United States Patent [19]

Tsuchiya

[11] Patent Number: 5,529,065
[45] Date of Patent: Jun. 25, 1996

[54] METHOD FOR MEASURING SCATTERING MEDIUM AND APPARATUS FOR THE SAME

[75] Inventor: Yutaka Tsuchiya, Hamamatsu, Japan

[73] Assignee: Hamamatsu Photonics K.K., Hamamatsu, Japan

[21] Appl. No.: 251,969

[22] Filed: Jun. 1, 1994

[30] Foreign Application Priority Data

Jun. 2, 1993 [JP] Japan .................................. 5-132214
Apr. 25, 1994 [JP] Japan .................................. 6-086737

[51] Int. Cl.$^6$ ...................................................... A61B 5/00
[52] U.S. Cl. ...................................................... 128/633
[58] Field of Search .................................. 128/633, 664, 128/665

[56] References Cited

U.S. PATENT DOCUMENTS

| | | | |
|---|---|---|---|
| 5,037,695 | 10/1991 | Hirao et al. | 128/633 |
| 5,277,181 | 1/1994 | Mendelson et al. | 128/633 |
| 5,285,783 | 2/1994 | Secker | 128/633 |
| 5,297,548 | 3/1994 | Pologe | 128/633 |
| 5,333,610 | 8/1994 | Hirao | 128/633 |
| 5,372,135 | 12/1994 | Mendelson et al. | 128/633 |

FOREIGN PATENT DOCUMENTS

| | | | |
|---|---|---|---|
| 64-88340 | 4/1989 | Japan . | |
| 1174940 | 7/1989 | Japan . | |
| 4110751 | 4/1992 | Japan . | |
| 2228314 | 8/1990 | United Kingdom . | |
| 8912223 | 12/1989 | WIPO . | |
| 9221283 | 12/1992 | WIPO | 128/633 |

OTHER PUBLICATIONS

Brian Wilson et al, "Optical Reflectance and Transmittance of Tissues: Principles and Applications", pp. 2186–2199, vol. 26, No. 2, IEEE J. Quantum Electron, 1990.

I. Oda et al, "Non-invasive Hemoglobin Oxygenation Monitor and Computed Tomography by NIR Spectrophotometry", pp. 284–293, SPIE, vol. 1431, 1991.

M. S. Patterson et al, "Time-Resolved Reflectance and Transmittance for the Non-Invasive Measurement of Tissue Optical Properties", pp. 2331–2336, Applied Optics, vol. 28, No. 12, Jun. 15, 1989.

M. S. Patterson, "Applications of Time-Resolved Light Scattering Measurements to Photodynamic Therapy Dosimetry", pp. 62–75, SPIE, vol. 1203, 1990.

E. M. Sevick et al, "Time-Dependent Photon Migration Imaging", pp. 273–283, SPIE, vol. 1599, 1991.

Graaff et al, "Optical Properties of Human Dermis In Vitro and In Vivo", Applied Optics, vol. 32, No. 4, Feb. 1, 1993, pp. 435–447.

(List continued on next page.)

Primary Examiner—Angela D. Sykes
Assistant Examiner—Eric F. Winakur
Attorney, Agent, or Firm—Cushman Darby & Cushman

[57] ABSTRACT

A method of measuring internal information in a scattering medium and an apparatus for the same of the present invention measure internal information in the scattering medium by measuring light diffused during propagation in the scattering medium at outside of the scattering medium while receiving the influence of the scattering and absorption, and performing arithmetic processing to the measured values. At this time, the three or more kinds of the detected signals (measured values) detected at a plurality of distances between the light incident position and the photodetection point for the light having a plurality of predetermined wavelengths are processed by utilizing dependencies of the behavior of light diffused during propagation in the scattering medium and the resulting signal, i.e., a photodetection signal on characteristics such as a scattering constituent, or an absorption constituent in the scattering medium and their concentration. If the measurement is performed at a plurality of wavelenghts on an object to be measured, a ratio of absorption coefficients and a ratio of concentrations of specified absorptive constituents in scattering medium can be measured.

13 Claims, 14 Drawing Sheets

OTHER PUBLICATIONS

Farrell et al, "The Use of a Neural Network to Determine Tissue Optical Properties From Spatially Resolved Diffuse Reflectance Measurements", Physics in Medecine and Biology, vol. 37, No. 12, pp. 2281–2286.

Farrell et al, "A Diffusion Theory Model of Spatially Resolved, Steady–State Diffuse Reflectance for the Noninvasive Determination of Tissue Optical Properties In Vivo", Med. Physics, vol. 19, No. 4, Jul. 1992, pp. 879–888.

METHOD FOR MEASURING SCATTERING MEDIUM AND APPARATUS FOR THE SAME

BACKGROUND OF THE INVENTION

1. Field of the Invention

The present invention relates to non-invasive measurement of internal information in a scattering medium by causing pulsed light, square wave light, or continuous light to be incident on a scattering medium such as a living body, and detecting light propagating in the scattering medium. More particularly, the present invention relates to a method for measuring internal information in a scattering medium and an apparatus for the same, which are capable of measuring a ratio of absorption coefficients and a ratio of concentrations of specific absorptive constituents in the scattering medium, its time change, its spatial distribution, etc., and which are capable of improving measurement precision.

2. Related Background Art

Demands for measurement of an absorption constituent in a scattering medium such as a living body or improvement of the measurement are very strong, and there are several reports and attempts therefor. The main prior art are listed at the end of this section.

In general, since light is scattered and/or absorbed at random in a scattering medium, light does not propagate straight. For the scattering medium in which the absorption is zero, a total quantity of light never decreases, but since light is scattered by scattering constituents at random, light propagates in a zigzag manner. In this case, a distance that light can propagate without the effect of the scattering is called a mean free path or a mean diffusion length, which is an inverse of a transport scattering coefficient $\mu_s'$. In the case of the living body specimen, the mean free path is about 2 mm. This is taught by Wilson Olsby Optical Reflectance and Transmittance of Tissues: Principle and Application, IEEE, J. Quantum Electron., Vol. 26, No. 12, pp. 2186–2199 (1990). In addition, the scattering medium comprises absorptive constituents other than the scattering constituents, so that the absorption occurs in accordance with a distance that light propagates while scattering, and the quantity of light is exponentially attenuated in accordance with the distance.

As prior art in the field of precise measurement of an absorption coefficient or a transport scattering coefficient of a scattering medium, it is necessary to measure the quantity of transmitted light or reflected light corresponding to continuous incident light or pulsed incident light, and it is necessary to measure transmitted light or reflected light corresponding to the pulsed incident light and to analyze its waveform. The former utilizes a measurement of the absorbance in which the Lambert-Beer Law is a basic principle. Here, the Lamber-Beer law is that the absorbance of the specimen is proportional to the product of the molar absorption coefficient, molar concentration, and a specimen thickness, and that a difference between the absorbances is proportional to a difference between the concentrations where a thickness of the specimen is constant.

However, in the case of the absorbance measurement in the scattering medium, a mean optical pathlength of light diffused during propagation between a light incident position and a photodetection point is varied depending on the absorption coefficient $\mu_a$ of the scattering medium. Therefore, in the absorbance measurement corresponding to the scattering medium in which the optical pathlength is constant, absorption coefficient dependency of the mean optical pathlength is a big problem, which hinders the precise measurement of an absorption coefficient or the concentration of an absorptive constituent, or if the measurement is performed, due to large errors in measurement, it cannot practically be used. For example, according to "Japanese Patent Application No. Sho 62-248590", "Japanese Patent Application No. Sho 62-336197", and "Japanese Patent Application No. Hei 2-231378", since a basic principle is to measure an optical coefficient in which an optical pathlength is assumed to be constant, errors in measurement caused by a change of the above-described optical pathlength cannot be avoided.

There is another method utilizing a mean optical pathlength which is measured by another method in the case of an absorbance measurement, but hence a mean optical pathlength is varied depending on the absorption coefficient, errors caused by approximating the mean optical pathlength to be a constant value cannot be avoided. Further, there are a method of measuring an absorbance difference using pulsed light, a method further utilizing a principle of dual-wavelength spectroscopy, and a method of measuring an absorbance using lights having three or more kinds of wavelengths, but in either case, since a method of measuring an absorbance optical density in which an optical pathlength in a scattering medium is assumed to be constant is applied, errors caused by the change of the optical pathlength occur in all cases, which hinders sufficient precise measurement.

In the prior art not based on an absorbance measurement, a method, in which transmitted light or reflected light is measured by time-resolved measurement using pulsed light or modulated light to analyze waveforms, has disadvantages that owing to the time-resolved measurement, a measurement method and an apparatus are very complicated and that the apparatus is expensive, as compared with a measurement method and an apparatus of the present invention in which quantity of light, that is, time integration of an optical signal is measured. There are several attempts for measuring internal absorption information by measuring reflected light or transmitted light upon the incidence of pulsed light to the medium by the time-resolved measurement and analyzing its waveform. Such is disclosed in Patterson et al., Time Resolved Reflectance and Transmittance for the Non-Invasive Measurement of Tissue Optical Properties, Applied Optics, Vol. 28, No. 12, pp. 2331–2336 (1989); Patterson et al., Application of Time-Resolved Light Scattering Measurements to Photodynamic Therapy Dosimetry, Proc. SPIE, Vol. 1203, pp. 670–675 (1990); and Sevick et al., Time-Dependent Photon Migration Imaging, Proc. SPIE, Vol. 1599, pp. 273–283 (1991). A measured optical signal has a long decay tail by the influence of scattering and absorption constituents. Patterson et al. assumes a model of uniform scattering medium to analytically obtain the light signal output[3]. A wave representing a time change in intensity of the optical output signal given by the formula defined by patterson et al. matches a waveform obtained by an experiment using a uniform scattering medium. According to Patterson et al. and the results of the experiment by the inventors of the present application, the absorption coefficient of absorptive constituents in the scattering medium is given by slope of waveform (differential coefficient) obtained when the optical signal is sufficiently attenuated, i.e., when a sufficiently long period has elapsed. However, because the optical signal at a location where an absorption coefficient is obtained required to be sufficiently attenuated means that the signal is very feeble, a signal to noise ratio (S/N ratio) of the signal to be measured is decreased, and consequently errors in measurement are increased. Therefore, it is hard to use in practical application. There are several kinds of attempts other than the above, but none of them give sufficient measurement precision.

References

1) B. C. Wilson and S. L. Jacques: Optical Reflectance and Transmittance of Tissues: Principle and Application, IEEE J. Quantum Electron., Vol. 26, No. 12, pp. 2186–2199 (1990)
2) I. Oda, Y. Ito, H. Eda, T. Tamura, M. Takada, R. Abumi, K. Nagai, H. Nakagawa, and M. Tamura; Non-invasive hemoglobin oxygenation monitor and computed tomography by NIR spectrophotometry, Proc. SPIE, Vol. 1431, pp. 284–293 (1991)
3) M. S. Patterson, B. Chance, and B. C. Wilson: Time resolved reflectance and transmittance for the non-invasive measurement of tissue optical properties, Applied Optics, Vol. 28, No. 12, pp. 2331–2336 (1989)
4) M. S. Patterson, J. D. Moulton, B. D. Wilson, and B. Chance: Application of time-resolved light scattering measurements to photodynamic therapy dosimetry, Proc. SPIE, Vol. 1203, pp. 62–75 (1990)
5) E. M. Sevick, N. G. Wang, and B. Chance: Time-dependent photon imaging, Proc. SPIE, Vol. 1599, pp. 273–283 (1991)

SUMMARY OF THE INVENTION

Measurement methods and measurement apparatus in the above-described field which have been developed and reported have not satisfied the measurement precision needed. The inventor of the present application theoretically and experimentally analyzed and examined the behavior of light in a scattering medium, which is a basis of the measurement in the above-described field. The inventor found that the conventional analysis methods are insufficient to described the complicated behavior of light in the scattering medium, and that most of approximations used in the process of deriving a principle of the measurement of the conventional measurement methods and the measurement apparatus do not hold in the actual object to be measured and the measurement field, which results in large errors included in the measured value. It is an object of the present invention to provide a new measurement method and a measurement apparatus which enhance the measurement precision while the errors are drastically decreased based on the above analyses, examinations, and experiments.

A method of measuring internal information in a scattering medium and an apparatus for measuring an absorption coefficient of the scattering medium and the information related to specified absorptive constituents utilizes new knowledge in which a change of optical pathlengths is taken into consideration. That is, a plurality of simultaneous relations between photodetection signals (measured values) when light having a predetermined wavelenght is diffused while propagation in the scattering medium and reaches at predetermined photodetection points and a plurality of known parameters are considered.

A method of measuring a scattering medium comprises (a) a step of causing light having a plurality of predetermined wavelenghts at which the scattering coefficient to the scattering medium is almost equal to be incident on the scattering medium, (b) a step of detecting light having the predetermined wavelenghts diffused during propagation in the scattering medium at detection points corresponding to a plurality of points where the distance between a light incidence position and a photodetection point is different to obtain three or more detected signals, and (c) a step of extracting internal information in the scattering medium by performing arithmetic processing to the detected signals utilizing three or more simultaneous relations between a scattering characteristic and an absorption characteristic on a diffusion-propagation path in the scattering medium when the light having the predetermined wavelengths is diffused during propagation and reaches at the detection points, and the detected signals.

Here, the light having the predetermined wavelength may be light having two or more wavelenghts, each having a different absorption coefficient to a specified absorptive constituent of the scattering medium, and the arithmetic processing may comprise a process of extracting primary internal information in the scattering medium obtained by the measurement with one predetermined wavelength, and a process of extracting secondary internal information in the specified constituent of the scattering medium utilizing the primary internal information.

An apparatus for measuring a scattering medium comprises (a) light-emitting means for emitting light having a plurality of predetermined wavelenghts having almost the same scattering coefficients to the scattering medium, (b) light-incident means for causing the light having the predetermined wavelenghts to be incident on the scattering medium, (c) photodetecting means for detecting light having the predetermined wavelenghts, diffused during propagation in the scattering medium at photodetection points corresponding to a plurality of points where the distance between a light incidence position and a photodetection point is different, and obtaining three or more detected signals, and (d) arithmetic processing means for extracting internal information in the scattering medium by performing arithmetic processing to the detected signals, utilizing three or more simultaneous relations among a scattering characteristic and an absorption characteristic on a diffusion-propagation path in the scattering medium when the light having the predetermined wavelengths is diffused during propagation and reaches at the detection points, and the detected signals.

Here, light having the predetermined wavelengths may be light having two or more wavelenghts, each having a different absorption coefficient to a specified absorptive constituent of the scattering medium, and the arithmetic processing means may execute a process of extracting primary internal information in the scattering medium obtained by the measurement with one kind of the predetermined wavelength, and a process of extracting secondary internal information in the specified constituent of the scattering medium utilizing the primary internal information.

A method of measuring internal information in a scattering medium and an apparatus for the same of the present invention measure internal information in the scattering medium by measuring light diffused during propagation in the scattering medium at outside of the scattering medium while receiving the influence of the scattering and absorption, and performing arithmetic processing to the measured values. At this time, the three or more detected signals (measured values) detected at a plurality of distances between the light incident position and the photodetection point for the light having a plurality of predetermined wavelengths are processed by utilizing a characteristic that the behavior of light diffused during propagation in the scattering medium and the resulting signal, i.e., a photodetection signal depend on characteristics and the concentration of a scattering constituent, or an absorption constituent in the scattering medium. If the measurement is performed at a plurality of places on an object to be measured, the spatial distribution of the information can be measured, and if the measurement is performed at different time, the time-change in the internal information can be measured.

In particular, in the method and apparatus of the present invention, it can be considered that the plurality of the predetermined wavelengths have the same transport scattering coefficients for the scattering constituents contained in the scattering medium, or that if they have the different transport coefficients, the difference is small enough to be neglected, and their absorption coefficients are selected to be different for the specified absorptive constituents. Then, light having the predetermined wavelengths is incident on the scattering medium, and light diffused during propagation in the scattering medium is detected at a plurality of distances between a light incident position and a photodetection point to obtain three or more detected signals (measured values). Next, the three or more detected signals and the known parameters are processed to measure the internal information in the scattering medium based on the three or more simultaneous relations of scattering and absorption when the light having the predetermined wavelengths reaches at the photodetection points, and the detected signals (measured values). The relation among the detected signals (measured values) and the various parameters, and the internal information in the scattering medium which is disclosed in the present application for the first time, is used in the measurement.

In the above cases, a method using one light incidence position and two photodetection points for light having a plurality of predetermined wavelenghts, a method using two light incidence positions and one photodetection point, and others are available. For the actual living body specimen, the plurality of the predetermined wavelengths can be selected so as to have the same scattering coefficients or to have the negligible scattering coefficients if they are different.

Therefore, a problem of errors in measurement caused by the change of optical pathlength is solved. Further, since the present invention is not the time-resolved measurement method, but is a method of measuring the quantity of light, that is, the rime integration value of a photodetection signal, the structure of the apparatus is very simple. Accordingly, the measurement or the monitoring of the concentration of oxygen in a brain of a human who is being operated on or exercising is made possible by the present invention.

As described above, according to the method of measuring internal information in the scattering medium and the apparatus for the same, the internal information in the scattering medium is measured at high precision by a simple apparatus structure, and a ratio of absorption coefficients at two wavelengths, internal information such as a ratio of concentration of the specified constituents, their spatial distributions, their time changes, and the distributions in a cross section can be measured. Moreover, since the measurement apparatus which utilizes the present invention uses the time integrated value of the optical signal, light utilization factor is high, and as the signal-to-noise ration is large, the measurement precision becomes high. Therefore, the measurement of the amount of oxygen in a brain, the amount of oxygen in a leg muscle of a human who is exercising or others can be made possible. Further, the non-invasive measurement of internal information of a human head, a body, a plant such as a standing tree, imaging of these, reconstruction of a tomogram or others can be made possible.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

DETAILED DESCRIPTION OF THE PREFERRED EMBODIMENTS

Figure 1:
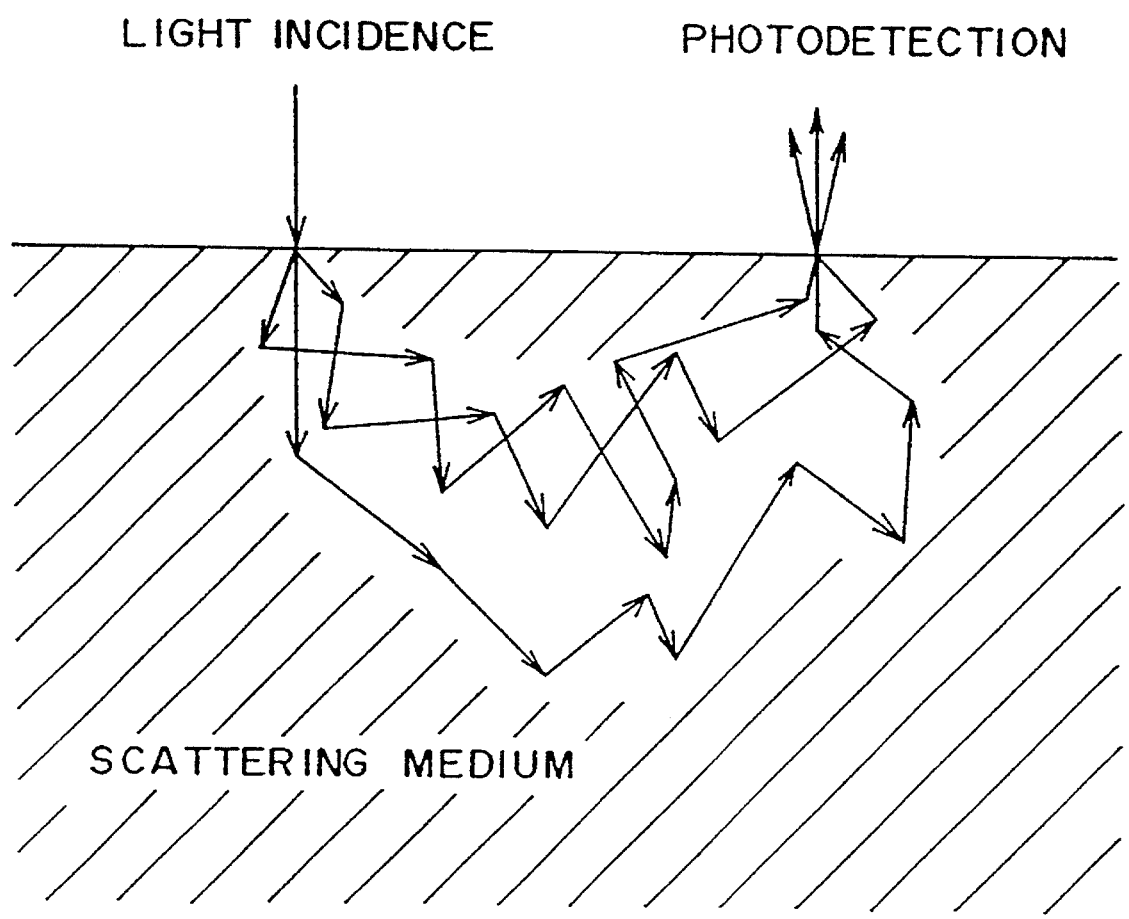
FIG. 1 is a view showing behavior of light in a scattering medium.

The embodiments of the present invention will be described in detail with reference to the accompanying drawings. The same parts are represented by the same reference numerals, and thus repetitive description is omitted.

(1) METHOD OF MEASURING INTERNAL INFORMATION OF SCATTERING MEDIUM

(1.1) Principle of Internal Information Measurement of Scattering Medium

Light is scattered, absorbed and diffused during propagation in a scattering medium such as a living body and some light components emerge on a surface of the scattering medium. That is, light is scattered and absorbed in the scattering medium, but also can be transmitted therethrough. For example, FIG. 1 shows behavior of light in the scattering medium and shows a state in which light is incident on one point of the scattering medium and diffusing light (reflected light) is detected at an other point. Light incident on the scattering medium is scattered at random and spreads all over the scattering medium, but in FIG. 1, only a track of photons detected by a photodetector is shown. In other words. FIG. 1 shows a track of photons which are utilized in practical measurement.

Figure 2:
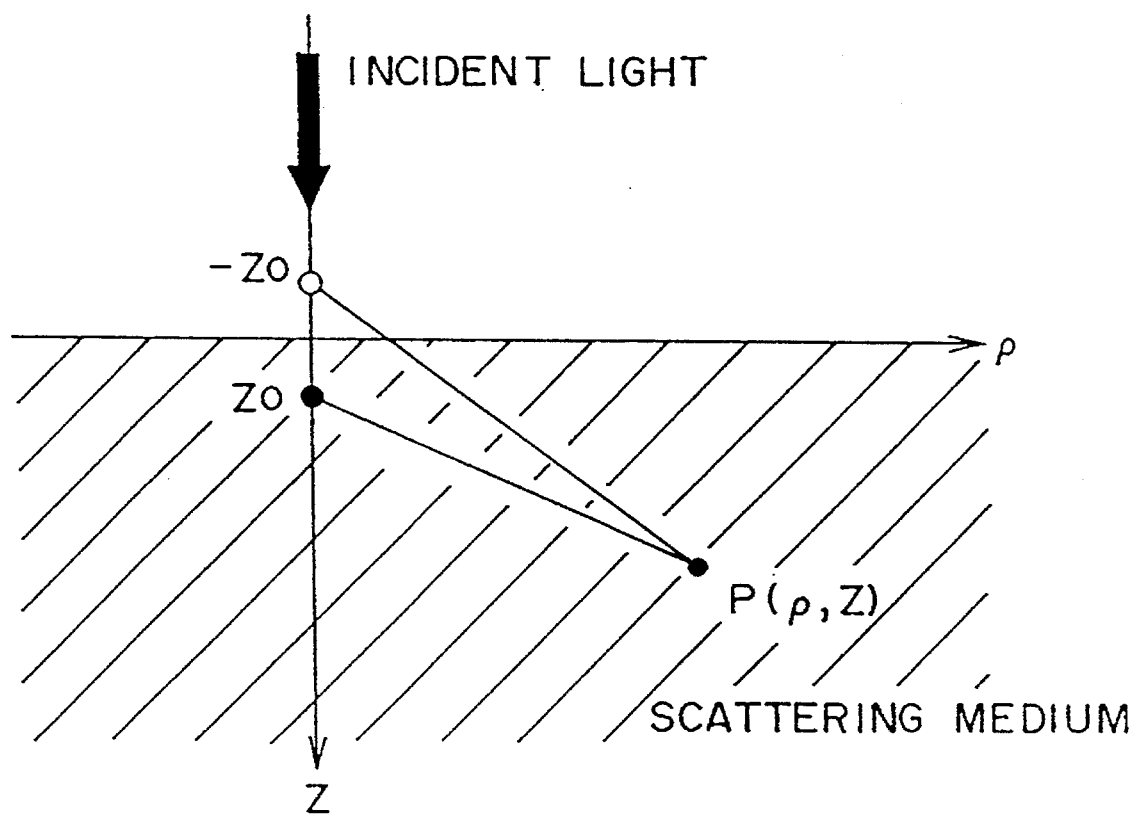
FIG. 2 is a view showing a way of obtaining quantity of detected light in a scattering medium.

It is known that the behavior of light in the scattering medium is precisely described and analyzed in accordance with a photon diffusion theory. According to the photon diffusion theory, a light pulse incident on the scattering medium is that its pulse width spreads as the light pulse is scattered, absorbed, and diffused during propagation in the scattering medium. FIG. 2 shows installation of a virtual light source to obtain quantity of light in the scattering medium. As shown in FIG. 2, when light is incident on a point ($\rho=0$, $z=0$) of a scattering medium surface, light may be detected at a point P ($\rho$, z) i.e., an optical signal is derived from a photon diffusion equation. In this case, since the photon diffusion is not present on the surface of the scattering medium and outside thereof, a boundary condition is required to be set to satisfy this requirement. Patterson et al. developed a method which satisfies the boundary condition by assuming a point light source of negative polarity and reported that the theoretical values obtained from this method and the experimental values are well matched. In FIG. 2, the point light source of negative polarity is set at a ○ mark ($\rho=0$, $z=-z_0$).

On the other hand, the behavior of each photon diffused during propagation in the scattering medium can be analyzed, experimented, and examined in accordance with Monte Carlo calculation with sue of a computer. In addition, the experiment can be conducted with a physical model of a scattering medium or a living body specimen. From the recent knowledge, the results derived from the photon diffusion theory, the results of Monte Carlo calculation, and the results of experiment with a sample are well matched. Therefore, it can be considered that the behavior of light in the scattering medium is sufficiently described by the photon diffusion equation. The various analyses, experiments, and examinations conducted by the present inventor and the recent accurate analyses and experiments of the behavior of light in the scattering medium confirm that the behavior of light in the scattering medium can precisely be described by the photon diffusion equation.

The photon diffusion equation which describes the behavior of light in the scattering medium as described above is, for example, expressed by a following equation using a photon fluence rate $\Phi$.

$$(1/c)(\partial \Phi(r,t)/\partial t) - D\nabla^2 \Phi(r,t) + \mu_a \Phi(r,t) = S(r,t) \quad (1,1)$$

where
$\Phi(r, t)$: the photon fluence rate at position r, at time t [photon/mm$^2$·sec] (r is vector)
D: the diffusion coefficient [mm]
$\mu_a$: the absorption coefficient [mm$^{-1}$]
c: the speed [mm/sec] of light in a scattering medium (given by a refractive index)
S(r,t): light source [photon/mm$^3$·sec].

Since an impulsed light source can be expressed by a delta function, a light impulse incident on an origin (r=0) at t=0 can be expressed by the following equation.

$$S(r, t) = \delta(r, t) = \delta(0, 0) = \delta(0) \cdot \delta(0) \quad (1.2)$$

Consequently, the photon diffusion equation corresponding to impulsed light is as follows:

$$(1/c)(\partial \Phi(r,t)/\partial t) - D\nabla^2 \Phi(r,t) + \mu_a \Phi(r,t) = \delta(0,0) \quad (1.3)$$

where $\delta(0,0)$ is a light impulse incident on an origin (r=0) at t=0.

The various optical constants on a scattering medium are, for
$\mu_S$: the scattering coefficient [mm$^{-1}$]
$\mu_S'$: the transport scattering coefficient [mm$^{-1}$]
$\mu_{tr}$: the transport attenuation coefficient [mm$^{-1}$]
$\mu_{eff}$: the effective attenuation coefficient [mm$^{-1}$]
g: the mean cosine $\theta$ of the scattering angle $\theta$, $$D = [3(\mu_a + \mu_s')]^{-1} = (3\mu_{tr})^{-1} \quad (1.4a)$$
$$\mu_s' = (1-g)\mu_s \quad (1.4b)$$
$$\mu_{tr} = \mu_a + \mu_s' = \mu_a + (1-g)\mu_s \quad (1.4c)$$

$$\mu_{eff} = [3\mu_a(\mu_a + \mu_s')]^{1/2} \quad (1.4d)$$
$$= \{3\mu_a[\mu_a + (1-g)\mu_s]\}^{1/2}.$$

In the case that a spot-like light pulse is incident on a semi-infinite scattering medium, a boundary condition is satisfied by providing a point light source of negative polarity at a location ($\rho=0$, $z=-z_0$) in accordance with Patterson et al. In general $z_0 \approx 1/\mu_s'$, but strictly speaking, it varies depending on a light incidence method or characteristics of scattering constituents in a scattering medium. This is confirmed by the inventors of the present application with use of Monte Carlo calculation. In the measurement method and the apparatus of the present invention, $z_0$ can be treated as an unknown value, which will be described later. Thus, no arguments about the uncertainty of $z_0$ or whether $z_0$ is a known or unknown value are needed. It is apparent that the method in which $z_0$ is treated as an unknown value is superior to the method in which $z_0$ is approximated to $z_0 = 1/\mu_s'$.

The photon diffusion equation (1.3) is solved under the above boundary condition, and an optical signal R($\rho$, 0, t)[photon/mm$^2$·sec] at an arbitrary location ($\rho$, 0) of the surface of the scattering medium is derived.

$$R(\rho, 0, t) = (4\pi D)^{-3/2} z_0 t^{-5/2} \cdot \exp[-(z_0^2 + \rho^2)/(4cDt)] \times \exp(-c\mu_a t) \quad (1.5)$$

Since the detected quantity of light I[$\rho$] is a result of the time integration of R($\rho$, 0, t), it is expressed by $$I[\rho] = \int_0^\infty R(\rho, 0, t) dt \quad (1.6)$$

and this equation can be solved with use of integral formulas to obtain $$I[\rho] = z_0[\mu_{eff}(z_0^2 + \rho^2)^{1/2} + 1]/[2\pi(z_0^2 + \rho^2)^{3/2}] \times \exp[-\mu_{eff}(z_0^2 + \rho^2)^{1/2}] \quad (1.7)$$

Taking the natural logarithm of I[$\rho$], $$\ln I[\rho] = \ln[z_0/(2\pi)] - (3/2)\ln(z_0^2 + \rho^2) + \quad (1.8)$$
$$\ln[\mu_{eff}(z_0^2 + \rho^2)^{1/2} + 1] - \mu_{eff}(z_0^2 + \rho^2)^{1/2}$$

Figure 3:
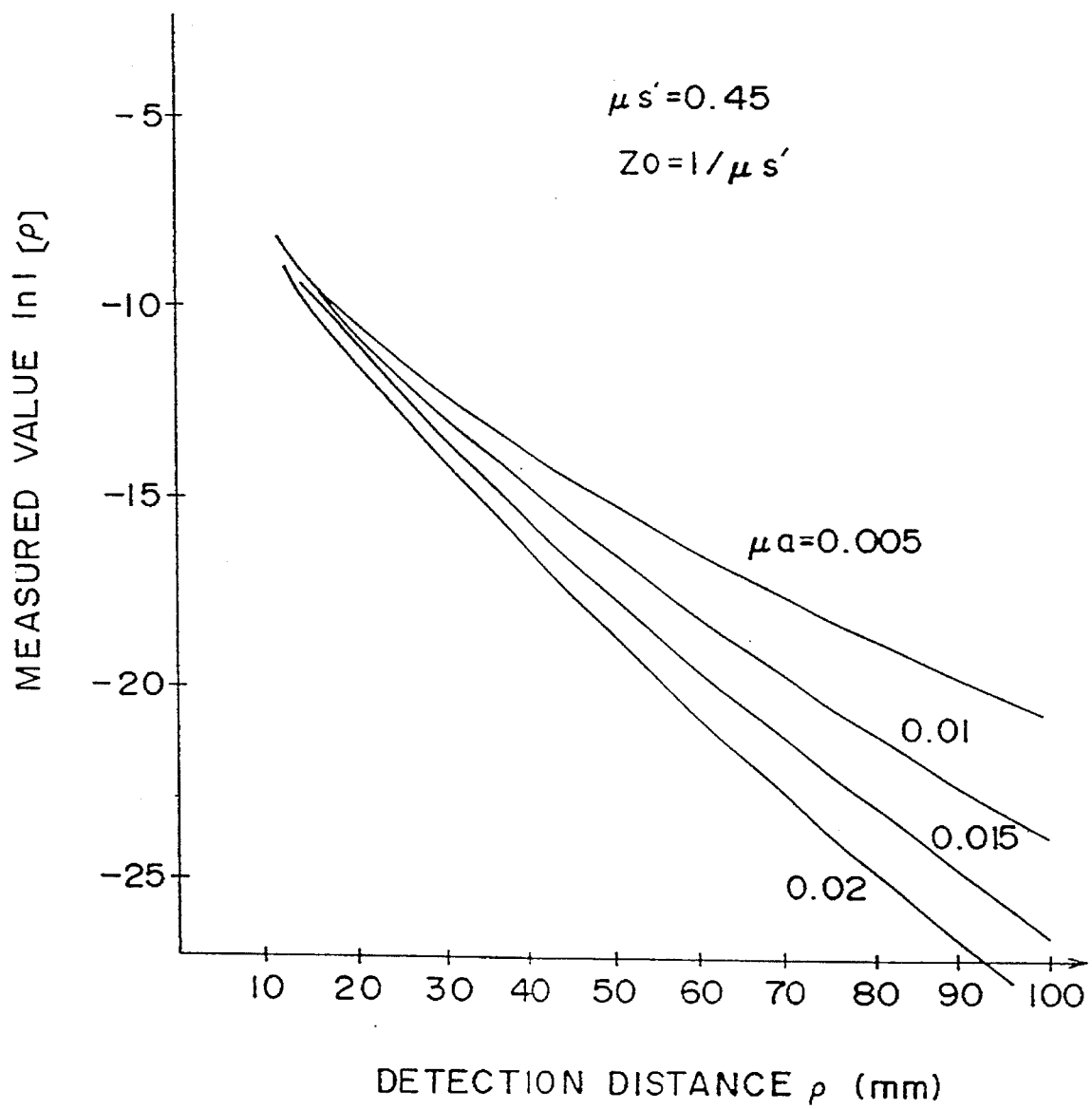
FIG. 3 is a graph showing relations between detected quantity of light $I(\rho)$ and detection distance $\rho$.

Therefore, $\mu_{eff}$ of the scattering medium can be calculated from equation (1.7) or (1.8) using the measurement value I[$\rho$], the known value $\rho$ and $z_0$. FIG. 3 shows a relation between the measurement value I[ρ] and a detection distance ρ. Here, $\mu_s'=0.45$ and $z_0=1/0.45$, and $\mu_a$ are shown as parameters. However, in practice, it is hard to know a precise value of $z_0$ as described above. In the present invention, the above-described basic knowledge is developed in the following application.

Figure 4:
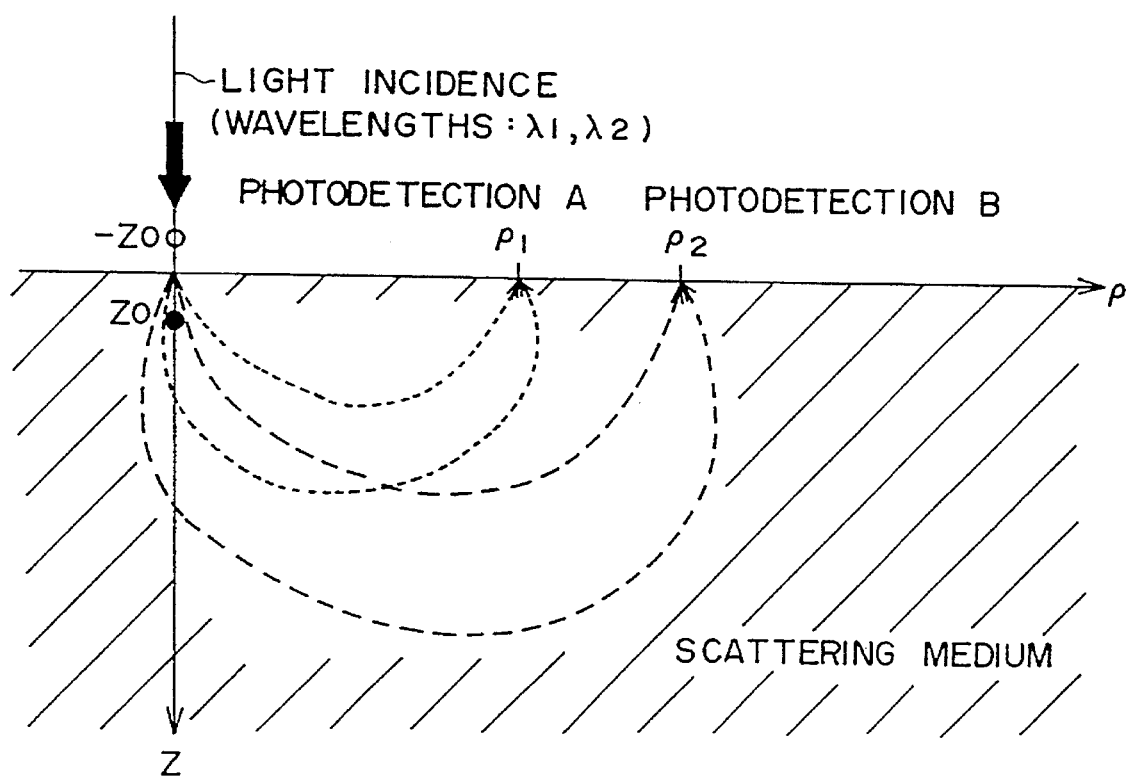
FIG. 4 is a view for explaining a principle of the present invention.

FIG. 4 shows a method of measuring scattering medium of the present invention. I[ρ] is measured using light having two different wavelenghts at two different points on a uniform scattering medium as shown in FIG. 4. Let two distances between a light incidence position and photodetection points (hereinafter simply called a detection distance) be $\rho_1$ and $\rho_2$, and two wavelengths be $\lambda_1$, and $\lambda_2$. Four kinds of measurement values are expressed as $I[\rho_1, \lambda_1]$: the measurement value at the detection distance $\rho_1$ and wavelengtth $\lambda_1$ $I[\rho_1, \lambda_2]$: the measurement value at the detection distance $\rho_1$ and wavelength $\lambda_2$ $I[\rho_2, \lambda_1]$: the measurement value at the detection distance $\rho_2$ and wavelength $\lambda_1$ $I[\rho_2, \lambda_2]$: the measurement value at the detection distance $\rho_2$ and wavelength $\lambda_2$.

Assuming that the transport scattering coefficients $\mu_s'$ and $z_0$ and the same for two kinds of wavelenghts $\lambda_1$ and $\lambda_2$, or a difference therebetween is extremely small if they are different, the absorption coefficients for the wavelenght $\lambda_1$ and $\lambda_2$ are expressed as $\mu_{a1}$ and $\mu_{a2}$, respectively. Then, the effective attenuation coefficients for the wavelenghts $\lambda_1$ and $\lambda_2$ are expressed as $$\mu_{eff1}=[3\mu_{a1}(\mu_{a1}+\mu_s')]^{1/2} \quad (1.9a)$$

$$\mu_{eff2}=[3\mu_{a2}(\mu_{a2}+\mu_s')]^{1/2} \quad (1.9b)$$

For, $\mu_{a1}$, $\mu_{a2}<<\mu_s'$, it can be expressed as $(\mu_{eff1}/\mu_{eff2})^2=\mu_{a1}/\mu_{a2}$ +tm (1.9c)

The measurement values for two detection distances and two wavelenghts satisfy the next four equations.

$$\ln I[\rho_1, \lambda_1] = \ln[z_0/(2\pi)] - (3/2)\ln(z_0^2 + \rho_1^2) + \quad (1.10a)$$
$$\ln[\mu_{eff1}(z_0^2 + \rho_1^2)^{1/2} + 1] - \mu_{eff1}(z_0^2 + \rho_1^2)^{1/2}$$

$$\ln I[\rho_1, \lambda_2] = \ln[z_0/(2\pi)] - (3/2)\ln(z_0^2 + \rho_1^2) + \quad (1.10b)$$
$$\ln[\mu_{eff2}(z_0^2 + \rho_1^2)^{1/2} + 1] - \mu_{eff2}(z_0^2 + \rho_1^2)^{1/2}$$

$$\ln I[\rho_2, \lambda_1] = \ln[z_0/(2\pi)] - (3/2)\ln(z_0^2 + \rho_2^2) + \quad (1.10c)$$
$$\ln[\mu_{eff1}(z_0^2 + \rho_2^2)^{1/2} + 1] - \mu_{eff1}(z_0^2 + \rho_2^2)^{1/2}$$

$$\ln I[\rho_2, \lambda_2] = \ln[z_0/(2\pi)] - (3/2)\ln(z_0^2 + \rho_2^2) + \quad (1.10d)$$
$$\ln[\mu_{eff2}(z_0^2 + \rho_2^2)^{1/2} + 1] - \mu_{eff2}(z_0^2 + \rho_2^2)^{1/2}$$

These equations (1.10a) to (1.10d) (hereinafter also generally called equation (1.10) are independent and the unknown values are three: $\mu_{eff1}$, $\mu_{eff2}$ and $z_0$. Consequently, the three unknown values $\mu_{eff1}$, $\mu_{eff2}$ and $z_0$ can be obtained from arbitrarily selected three equations from the above four equations. In general, it is not necessary to solve for $z_0$.

To obtain $\mu_{eff1}$, $\mu_{eff2}'$, and $z_0$, the three simultaneous equations may be of any forms as long as the equations are independent from each other and derived from equation (1.6) or (1.7). When $z_0$ can be treated as a known value, $\mu_{eff1}$ and $\mu_{eff2}$ can be obtained by solving the two simultaneous equations. The computation to solve such simultaneous equations can be performed at high speed using a computer.

Next, a case of $z_0<<\rho_1$, $\rho_2$ will be explained as one example of an approximate method. Since $z_0$ is generally about $1/\mu_s'$ to 2 mm, in the general measurement in which $\rho_1$ and $\rho_2$ are about 20 and 100 mm, $z_0<<\rho_1$, $\rho_2$. Equations (1.10) are now expressed as $$\ln I[\rho_1, \lambda_1]=\ln[z_0/(2\pi)]-3\ln\rho_1+\ln[\rho_1\cdot\mu_{eff1}+1]-\rho_1\cdot\mu_{eff1} \quad (1.11a)$$

$$\ln I[\rho_1, \lambda_2]=\ln[z_0/(2\pi)]-3\ln\rho_1+\ln[\pi_1\cdot\mu_{eff2}+1]-\rho_1\cdot\mu_{eff2} \quad (1.11b)$$

$$\ln I[\rho_2, \lambda_1]=\ln[z_0/(2\pi)]-3\ln\rho_2+\ln[\rho_2\cdot\mu_{eff1}+1]-\rho_2\cdot\mu_{eff1} \quad (1.11c)$$

$$\ln I[\rho_2, \lambda_2]=\ln[z_0/(2\pi)]-3\ln\rho_2+\ln[\rho_2\cdot\mu_{eff2}+1]-\rho_2\cdot\mu_{eff2} \quad (1.11d)$$

The effective attenuation coefficients $\mu_{eff1}$ and $\mu_{eff2}$ are expressed by equations (1.9a) and (1.9b). Therefore, $\mu_{eff1}$, $\mu_{eff2}$ and $z_0$ can be obtained in the same manner as described above.

From equations (1.11) (equation (1.11a) to equation (1.11d)) equations (1.12a) and (1.12b)

$$\ln(I[\rho_1, \lambda_1]/I[\rho_2, \lambda_1])=\ln[(\rho_1\cdot\mu_{eff1}+1)/(\rho_2\cdot\mu_{eff1}+1)]-3\ln(\rho_1/\rho_2)-(\rho_1-\rho_2)\mu_{eff1} \quad (1.12a)$$

$$\ln(I[\rho_1, \lambda_2]/I[\rho_2, \lambda_2])=\ln[(\rho_1\cdot\mu_{eff2}+1)/(\rho_2\cdot\mu_{eff2}+1)]-3\ln(\rho_1/\rho_2)-(\rho_1-\rho_2)\mu_{eff2} \quad (1.12b)$$

are obtained. $z_0$ is eliminated in equations (1.12) (equation (1.12a) and equation (1.12b)), $\mu_{eff1}$ and $\mu_{eff2}$ can be obtained using the known values $\rho_1$ and $\rho_2$, and for $\mu_{a1}$, $\mu_{a2}<<\mu_s'$, $\mu_{a1}/\mu_{a2}$ is obtained from equation (1.9c).

For $\rho_1\mu_{eff1}, \rho_1\mu_{eff2}, \rho_2\mu_{eff1}, \rho_2\mu_{eff2}>>1$, equations (1.12) are expressed as $$\ln(I[\rho_1, \lambda_1]/I[\rho_2, \lambda_1])=-2\ln(\rho_1/\rho_2)-(\rho_1-\rho_2)\mu_{eff1} \quad (1.13a)$$

$$\ln(I[\rho_1, \lambda_2]/I[\rho_2, \lambda_2])=-2\ln(\rho_1/\rho_2)-(\rho_1-\rho_2)\mu_{eff2} \quad (1.13b)$$

Use equation (1.9c) to obtain, $$\mu_{a1}/\mu_{a2}=\{\ln(\rho_1^2I[\rho_1, \lambda_1]/(\rho_2^2I[\rho_2,\lambda_1]))\div\ln(\rho_1^2I[\rho_1, \lambda_2]/(\rho_2^2I[\rho_2\lambda_2])\}^2 \quad (1.14)$$

The value of $\mu_{a1}/\mu_{a2}$ can simply be obtained.

The calculation to obtain the value of $\mu_{a1}/\mu_{a2}$ may use any simultaneous equations (1.10), (1.11), (1.12) and (1.13) and can be calculated at high speed using a computer. The equation for obtaining the value of $\mu_{a1}/\mu_{a2}$ may be of any forms as long as the equation is derived from equation (1.6). Such $\mu_{a1}/\mu_{a2}$ is utilized in the measurement of the degree of oxygen saturation of hemoglobin, which will be described later.

Figure 5:
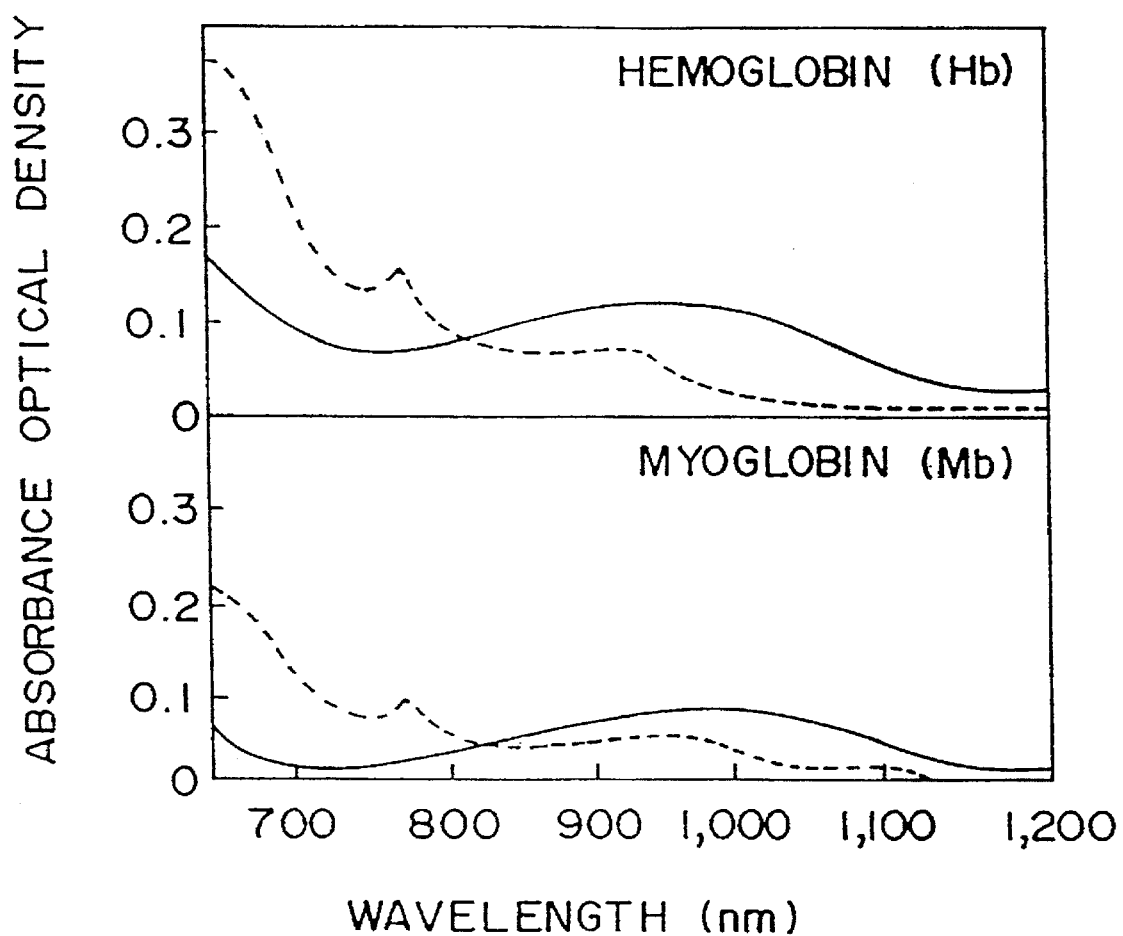
FIG. 5 is a graph showing absorption spectra of respective biological material.

In the dual-wavelength spectroscopy measurement, wavelength dependency of the absorption coefficient of the absorptive constituents in the scattering medium is used. For example, in the measurement of oxyhemoglobin and reduced hemoglobin, and oxymyoglobin and reduced myoglobin, the absorption spectra of which are shown in FIG. 5, light having a wavelenght in which the absorption coefficient difference between oxidation and deoxidation is large, that is, light having 700 nm to 1.2 μm wavelenght is frequently used. It is assumed that the scattering coefficients of the scattering constituents for light having two different wavelengths are the same or that the difference therebetween is extremely small if they are different, but for the living body specimen, the wavelength can be selected so that the difference is negligible. The reliability and the propriety of the results described above are confirmed by Monte Carlo calculation and the experiments by the inventors of the present application.

The present invention utilizes the integral value of the detected optical signal, so that the light pulse having a various waveform can be utilized as long as the integral time can be specified. For example, the square wave or continuous light is apparently suitable. If the measurement is performed with lights having three or more kinds of wavelengths or at three or more kinds of detection distances, improvement in the measurement precision and/or measurement of specimens which have background absorption are possible. In FIG. 4, light is incident on one incidence position and lights are detected at the two different points, but a method in which light is incident on two different positions and light is detected at one photodetection point can also accomplish the above measurement. The combination of the light incidence position and the photodetection point is of various kinds.

The case that the object to be measured is a semi-infinite scattering medium has been explained; however, in practice, a finite scattering medium is mostly measured. In this case, the boundary condition should be satisfied at the surface of the scattering medium shown in FIG. 4, and the condition of light diffusion should hold in most of lights which are diffused during propagation in the scattering medium. This condition holds when the scattering medium is considered to be sufficiently large as compared with detection distances $\rho_1$ and $\rho_2$. For example, the region in the curved lines in FIG. 4 shows a region through which most of lights pass. The presence of such a region is apparent from a spindle-shaped beam in the scattering medium reported by Sevick et al. or the results of Monte Carlo calculation.

When the thickness (z direction) of the scattering medium is not considered to be sufficiently large as compared with the photodetection distances $\rho_1$ and $\rho_2$, second point light sources of negative polarity and positive polarity which satisfy the boundary condition may be installed on the back surface (surface opposition to the light incident plane) of the scattering medium. In this case, theoretically, in order to compensate the influence of the second point light sources of negative polarity and positive polarity, third point light sources of negative polarity and positive polarity are required and further in order to compensate the influence of the third point light sources, fourth point light sources of negative polarity and positive polarity are required. However, since the influence of the installed point light sources to the emitted light rapidly decreases in order, the influence can be approximately by finite point light sources. In this case, the above-stated equations (1.5) to (1.10) are the equations to which terms related to the influence of the additional point light sources of negative polarity and positive polarity are added. However, in this equation, only the number of terms is increased while the number of unknown values and the independence of every equation are unchanged. Thus, the same relation as described above can hold true.

Figure 6:
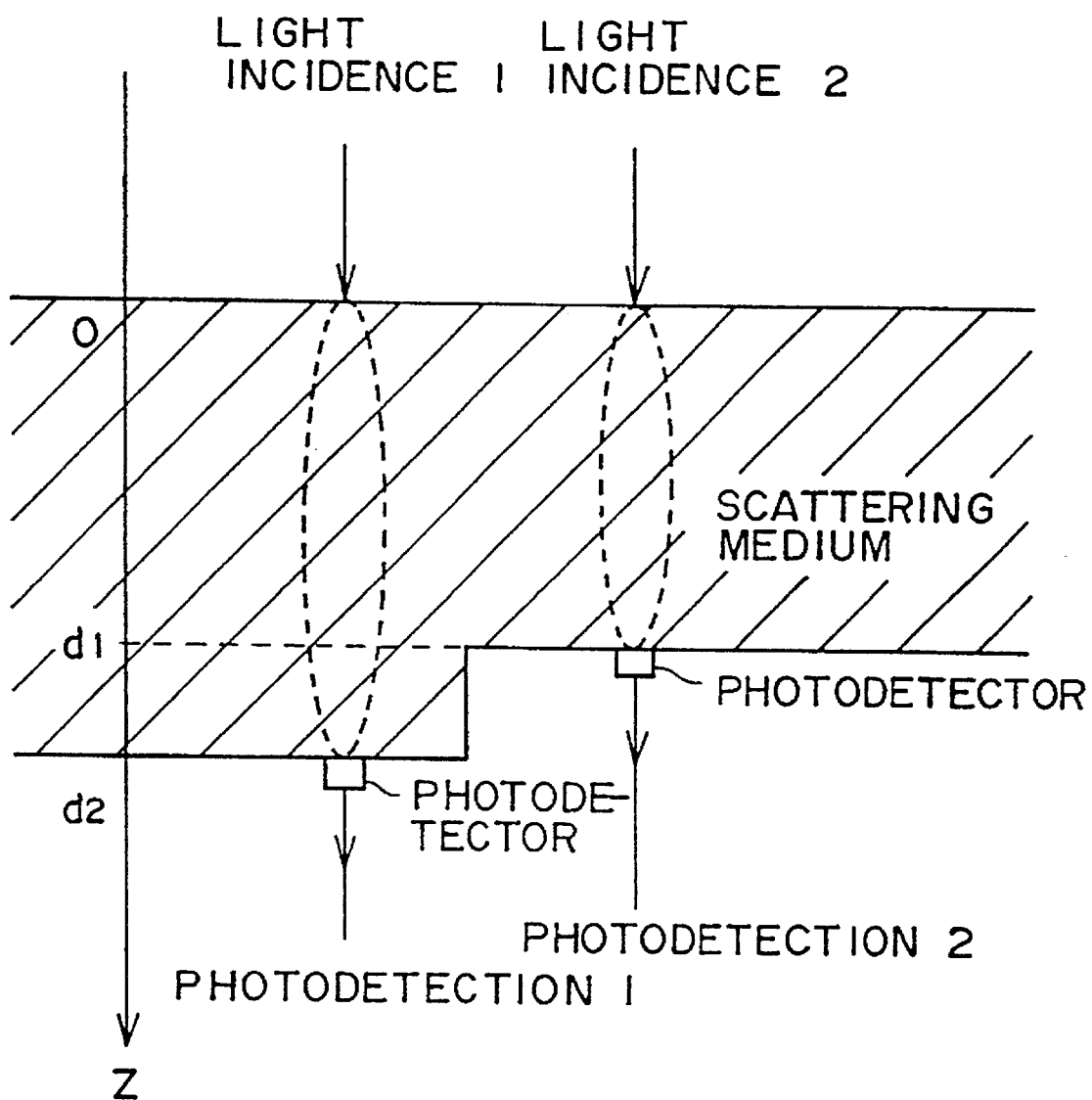
FIG. 6 is a view showing measurement of a slab-like specimen.
Figure 7:
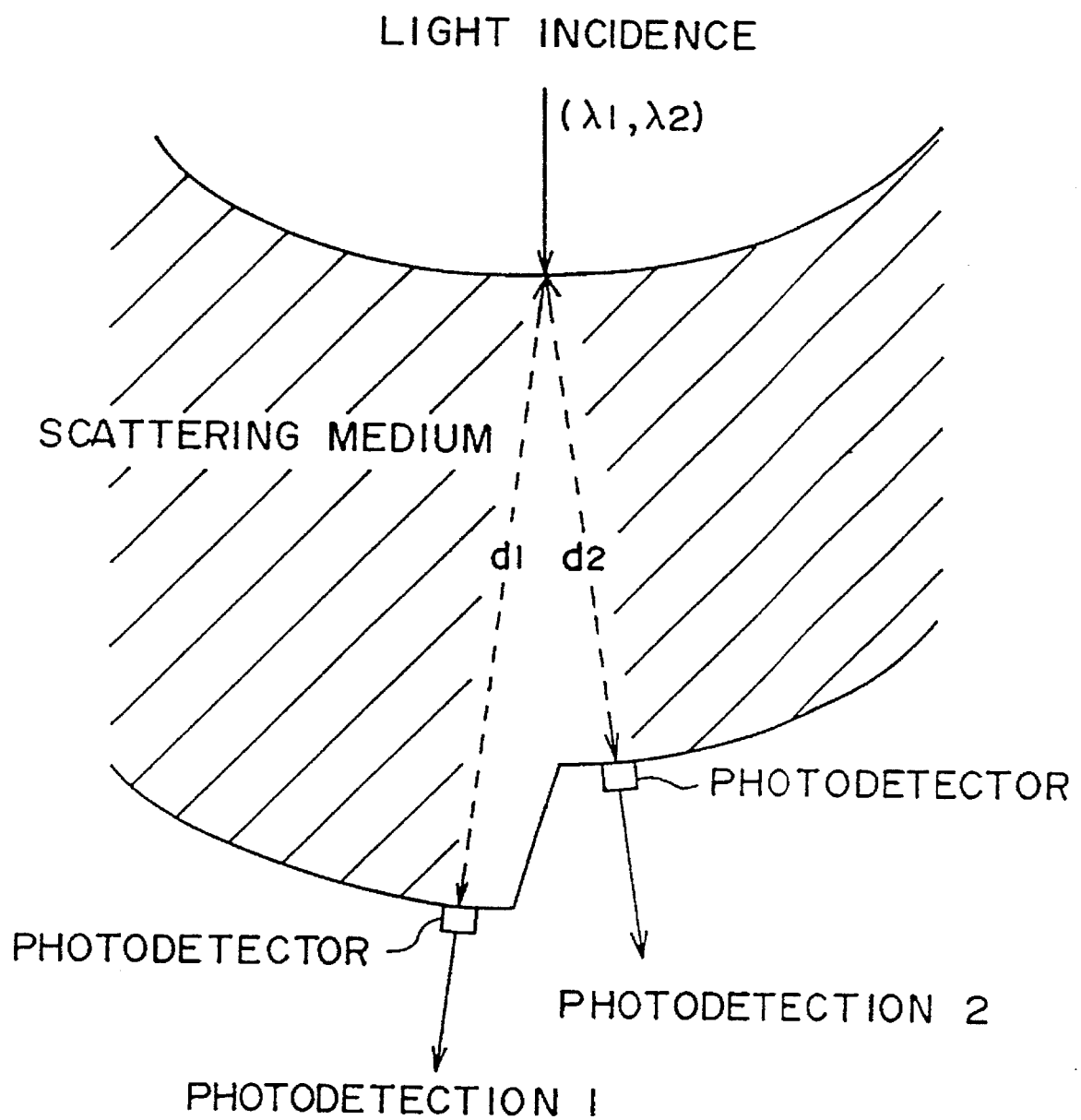
FIG. 7 is a view showing measurement of a slab-like specimen.

The measurement method and apparatus of the present invention can also be applied to a slab-like specimen, and its state is shown in FIG. 6 and FIG. 7. In FIG. 6, lights are incident on two positions and lights are detected at different points. In FIG. 7, light is incident on one position and lights are detected at different points of different detection distances. In the case of the slab-like specimen, assuming the detection distance is d, a result derived from the photon diffusion equation (1.3) which is equivalent to the above-stated equation (1.7) is, for example, $$I[d] = (z_0/\pi d^3)[(d\mu_{eff})^2 + 3d\mu_{eff} + 3]\exp(-d\mu_{eff}) \quad (1.15)$$

However, this equation is a modification form of equation (1.7), that is, the number of unknown values and the number of known values are the same and the parameters are also the same, so that similar to the above case, the equations can be modified and expanded to obtain four equations equivalent to equations (1.10).

Therefore, in the same way as described above, the three unknown values $\mu_{eff1}$, $\mu_{eff2}$ and $z_0$ can be obtained with use of the three measured values and the three equations arbitrarily selected from the above-stated four equations. Note that generally it is not necessary to be obtained $z_0$. The above calculation can be made with the equations in any form as long as the equations are derived from equation (1.15) and are independent of each other.

In the case of treating $z_0$ as a known number, $\mu_{eff1}$ and $\mu_{eff2}$ can be obtained by solving the simultaneous equations of two independent equations derived from equation (1.15). The internal information relating to the absorption constituents such as the degree of oxygen saturation of hemoglobin can be obtained by deriving the value of $\mu_{a1}/\mu_{a2}$. The calculation to solve such simultaneous equations is performed at high speed using a computer.

The internal information in the scattering medium, which is obtained by the measurement of the slab-like specimen as described above, is a mean value of the information along with a straight line connecting the light incidence position and the photodection point. Therefore, when the internal information is sufficiently diffused as compared with the distance between the photodection points as shown in FIG. 6 and FIG. 7, the simple imaging can be performed by considering these values as integral values along the straight line. Further, image reconstruction as in X-ray CT can be performed to obtain a tomogram associated with the internal information. Imaging of the degree of oxygen saturation of hemoglobin or myoglobin, or distribution of absorptive constituents, or reconstructions of tomogram can be performed. If the above-described measurement is performed at a different time, the measurement of the time change in the internal information is made possible. Such arithmetic processing can be performed at high speed using a computer unit which comprises a memory, a display, etc.

Errors in measurement in both the case of a method of the present invention and a conventional absorption method in which the average optical pathlength is assumed to be a constant will be explained to show one example of the effectiveness of the present invention.

Considering the scattering medium which occupies infinite spaces as shown in FIG. 4, the optical signal to be detected is expressed by equation (1.5). The average optical pathlength <L>, that is, the centroide of the waveform of the $R(\rho, 0, t)$ is expressed by the following equation:

$$<L> = \left[ c\int_0^\infty tR(\rho, 0, t)dt \right] / \left[ \int_0^\infty R(\rho, 0, t)dt \right] \quad (1.16)$$

$$= (3/2)(\mu_a + \mu_s')(z_0^2 + \rho^2)/[1 + (z_0^2 + \rho^2)^{1/2}\mu_{eff}].$$

Assuming that $\mu_s' = 0.45[\text{mm}^{-1}]$, $z_0 = 1/\mu_s'$, typical values for a living body specimen, and that $\rho = 50[\text{mm}]$ as the measurement condition, and that the average optical pathlengths are $<L(\mu_a = 0.01)>$ and $<L(\mu_a = 0.02)>$ when $\mu_a$ is changed from 0.01 to 0.02, respectively, and that the average optical pathlength is a constant, error $\Delta$ in the average optical pathlength is given by $$\Delta = \{<L(\mu_a = 0.01)> - <L(\mu_a = 0.02)>\}/<L(\mu_a = 0.01)> \times 100 \approx 14(\%). \quad (1.17)$$

Consequently, the absorbance optical density obtained under the assumption that the average optical pathlength is constant has about a 14% error. On the contrary, the method of the present invention performs the arithmetic processing utilizing the relation in which the change of the optical pathlengths is taken into consideration, so that the errors as described above can be eliminated. The above description is the same in the case of the measurement of the slab-like scattering medium, and there is a small difference in the percentage of errors, but the effectiveness of the present invention is apparent.

(1.2) Measurement Method of Absorption Information

A method of obtaining the information relating to absorption or absorptive constituents based on the internal information obtained as described above by performing the arithmetic processing will be explained below.

(i) Measurement Method of Degree of Oxygen Saturation of Hemoglobin

The main absorptive constituents in a mammalian brain are water, cytochrome, oxyhemoglobin, and reduced hemoglobin. Absorption of water and cytochrome in a near-infrared rage is as small as negligible with respect to an oxyhemoglobin and a reduced hemoglobin. The oxyhemoglobin and the reduced hemoglobin have different absorption spectra, as shown in FIG. 5. The skull is regarded as scattering medium with respect to near-infrared rays.

The light having wavelenghts $\lambda_1$ and $\lambda_2$ is considered. Absorption coefficients corresponding to the wavelenghts $\lambda_1$ and $\lambda_2$ can be obtained in accordance with the Lambert-Beer law as follows:

$$\mu_{a1} = \epsilon_{Hb,1}[Hb] + \epsilon_{HbO,1}[HbO] \quad (2.1a)$$

$$\mu_{a2} = \epsilon_{Hb,2}[Hb] + \epsilon_{HbO,2}[HbO] \quad (2.1b)$$

where $\epsilon_{Hb,1}$: the molar absorption coefficient [mm$^{-1}$·M$^{-1}$] of the reduced hemoglobin at the wavelength $\lambda_1$ $\epsilon_{HbO,1}$: the molar absorption coefficient [mm$^{-1}$·M$^{-1}$] of the oxyhemoglobin at the wavelength $\lambda_1$ $\epsilon_{Hb,2}$: the molar absorption coefficient [mm$^{-1}$·M$^{-1}$] of the reduced hemoglobin at the wavelength $\lambda_2$ $\epsilon_{HbO,2}$: the molar absorption coefficient [mm$^{-1}$·M$^{-1}$] of the oxyhemoglobin at the wavelength $\lambda_2$

[Hb]: the molar concentration [M] of the reduced hemoglobin

[HbO]: the molar concentration [M] of the oxyhemoglobin

Since the degree Y of oxygen saturation is given by $$Y = [HbO]/([Hb] + [HbO]), \quad (2.2)$$

the following equation is obtained.

$$\mu_{a1}/\mu_{a2} = [\epsilon_{Hb,1} + Y(\epsilon_{HbO,1} - \epsilon_{Hb,1})] \div [\epsilon_{Hb,2} + Y(\epsilon_{HbO,2} - \epsilon_{Hb,2})] \quad (2.3)$$

Therefore, the degree Y of oxygen saturation is calculated using $\mu_{a1}/\mu_{a2}$ obtained from the above measurement and the known parameters $\epsilon_{Hb,1}$, $\epsilon_{HbO,1}$, $\epsilon_{Hb,2}$, and $\epsilon_{HbO,2}$. If a wavelength ($\approx$800 nm, isosbestic wavelength) which has the same absorption level for both an oxyhemoglobin and a reduced hemoglobin is used, the above equation can be made simpler.

(ii) Presence of Background Absorption

Background absorption may not be neglected in an living body. In this case, if the background absorption levels at the wavelengths $\lambda_1$, $\lambda_2$, and $\lambda_3$ are defined as $a_1$, $a_2$, and $a_3$, respectively, the following equations are established in accordance with the Lambert-Beer law.

$$\mu_{a1} = \epsilon_{Hb,1}[Hb] + \epsilon_{HbO,1}[HbO] + a_1 \quad (2.4a)$$

$$\mu_{a2} = \epsilon_{Hb,2}[Hb] + \epsilon_{HbO,2}[HbO] + a_2 \quad (2.4b)$$

$$\mu_{a3} = \epsilon_{Hb,3}[Hb] + \epsilon_{HbO,3}[HbO] + a_3 \quad (2.4c)$$

The above equations are rearranged to obtain the following equation:

$$(\mu_{a1} - \mu_{a2})/(\mu_{a3} - \mu_{a2}) = [(\mu_{a1}/\mu_{a2}) - 1]/[(\mu_{a3}/\mu_{a2}) - 1] \quad (2.5)$$
$$= [(\epsilon_{Hb,1} - \epsilon_{Hb,2}) Y(\epsilon_{HbO,1} - \epsilon_{HbO,2} - \epsilon_{Hb,1} + \epsilon_{Hb,2}) + K(a_1 - a_2)] \div [(\epsilon_{Hb,3} - \epsilon_{Hb,2}) + Y(\epsilon_{HbO,3} - \epsilon_{HbO,2} - \epsilon_{Hb,3} + \epsilon_{Hb,2}) + K(a_3 - a_2)]$$

$$\text{for } K = 1/([Hb] + [HbO]). \quad (2.6)$$

therefore, if the wavelengths are suitably selected so that $a_1 \approx a_2 \approx a_3$, in the same way as described above, the degree Y of saturation can be obtained by obtaining $(\mu_{a1}/\mu_{a2})$ and $(\mu_{a3}/\mu_{a2})$ using the measurement values at the lights having three kinds of wavelengths and the known parameters, and substituting $(\mu_{a1}/\mu_{a2})$, $(\mu_{a3}/\mu_{a3})$ and the known parameters into equation (2.5). Note that in the above condition, $a_1 \approx a_2 \approx a_3$ can be achieved by properly selecting a wavelength for the object to be measured such as a living body, but it is assumed that the scattering coefficients for the three wavelengths are the same.

Figure 8:
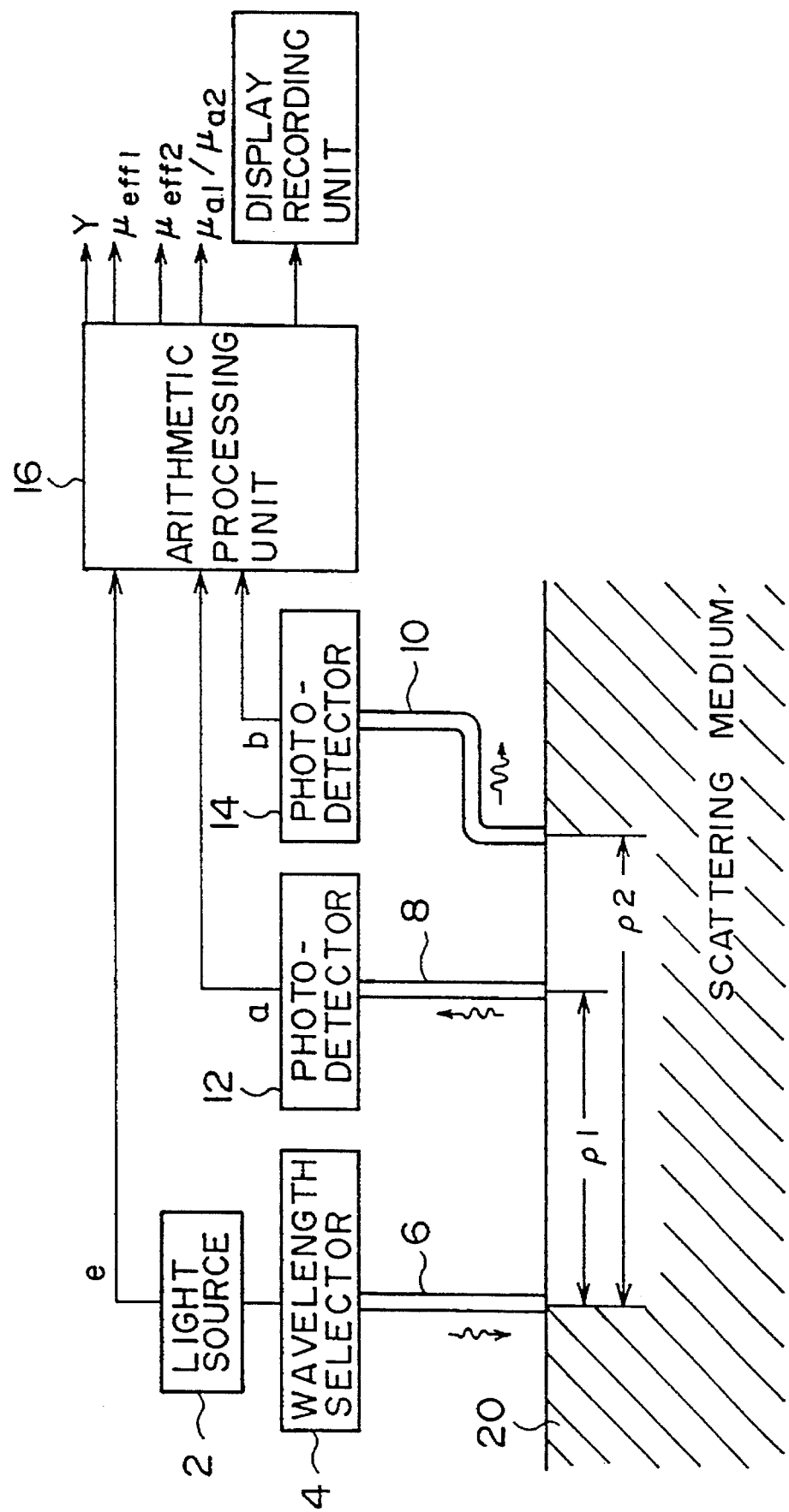
FIG. 8 is a view showing a configuration of an apparatus of the first embodiment.

(2) APPARATUS FOR MEASURING INTERNAL INFORMATION IN SCATTERING MEDIUM (2.1) First Embodiment of the Apparatus FIG. 8 illustrates the first structure of the apparatus for carrying out the method of measuring internal information in a scattering medium according to the present invention. A light source 2 using a laser diode or the like generates light having certain wavelengths $\lambda_1$ and $\lambda_2$. The wavelength of light from the light source must be appropriately selected in accordance with the object to be measured. A light having a wavelength of 700 nm or more is used mostly in association with absorption of a hemoglobin or the like. Since the oxyhemoglobin and the reduced hemoglobin have different absorption coefficients, as shown in FIG. 5, the oxyhemoglobin is distinguished from the reduced hemoglobin by selecting an appropriate wavelength before measurement. In this case, using light having three or more wavelengths, the measurement precision can be further improved. Various kinds of light sources such as a light emitting diode, a laser diode, an HeNe laser or others can be used. Further, the light source which generates pulsed light or square wave light as described above may be used.

A wavelength of light from the light source 2 is selected by a wavelength selector 4 and the light is incident on a surface of a scattering medium 20 which is an object to be measured through a light guide 6. In this case, there is another method utilizing a condenser lens or a pinhole, which will be described later. Since the average diffusion length is approximately 2 mm in the scattering medium as described above, the incident light is scattering before it propagates about 2 mm, and loses the original direction. Therefore, the influence of the average diffusion length in a few cm scattering medium can be neglected, sot hat spot-like light is incident on the scattering medium. Thick beam-like light may be cased to be incident on the scattering medium. This case is considered as a linear arrangement of a plurality of spot-like light sources.

A space between the light guide 6 and the object 20 to be measured is very small in the embodiment of FIG. 7. However, this space can be made large, and a liquid medium or a jelly-like object (hereinafter called an interface material) having substantially the same refractive index and scattering coefficient as the scattering medium 20, which is the object to be measured, may be filled in this space. Since the light is diffused during propagation in the interface material and is then incident on the object to be measured, no problems arise. If surface reflection from the scattering medium is a problem, the influence of the surface reflection or others can be reduced by properly selecting the interface material.

The light diffused during propagation in the scattering medium is received by light guides 8 and 10 provided on the position spaced apart from the light incident position by distances $\rho_1$ and $\rho_2$, respectively. The interface material may also be used for the same reasons as described above.

The first photodetector 12 and the second photodetector 14 convert the received optical signals into electric signals, amplify the electrical signals, and output the detected signals a and b, respectively. Various kinds of photodetectors such as a photomultiplier, a phototube, a photodiode, an avalanche photodiode, or a PIN photodiode can be used as the photodetectors 12 and 14. Any photodetector can be selected as long as it has spectral sensitivity to detect light of the specified wavelength. If an optical signal is very feeble, a high-gain photodetector is used. The other parts of the photodetector other than the light incident plane may preferably have the structure which absorbs or shields light. If light diffused during propagation in the scattering medium has light components having a plurality of wavelengths, a wavelength selection filter (not shown) is inserted between the photodetectors 12 and 14 and the scattering medium 20.

An arithmetic processing unit 16 processes the detected signals a and b from the first detector 12 and the second detector 14, and converts the signals a and b into the measurement values c and d in proportion to the detected quantity of light, respectively. In particular, the arithmetic processing unit 16 integrates the detected signals a and b in time by utilizing a signal e which is sychronized with the light generation of the light source 12. Note that when pulsed light is utilized, the synchronizing signal e may be omitted.

Next, the measurement values c and d at the wavelengths $\lambda_1$ and $\lambda_2$, and the known parameters $\rho_1$ and $\rho_2$ which are set or measured by another method are processed based on the three simultaneous equations to calculate the internal information in the scattering medium, that is, the effective attenuation coefficients $\mu_{\text{eff1}}$ and $\mu_{\text{eff2}}$ at the wavelengths $\lambda_1$ and $\lambda_2$, and the ratio of absorption coefficients, i.e., $\mu_{a1}/\mu_{a2}$. This sort of arithmetic processing can be operated at high speed by a micro computer installed in the arithmetic processing means. If desired, the degree of oxygen saturation of hemoglobin is calculated using the obtained internal information, i.e., the ratio of $\mu_{a1}$ and $\mu_{a2}$. If background absorption is present, light having three or more wavelengths as described above is used.

Figure 9:
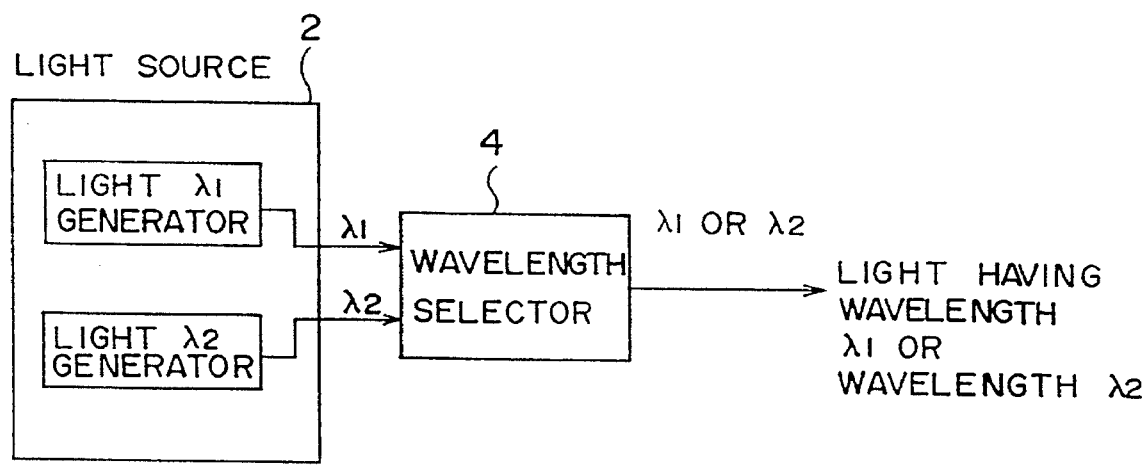
FIG. 9 and 10 are views respectively showing a configuration of switching or mixing lights having different wavelengths.
Figure 10:
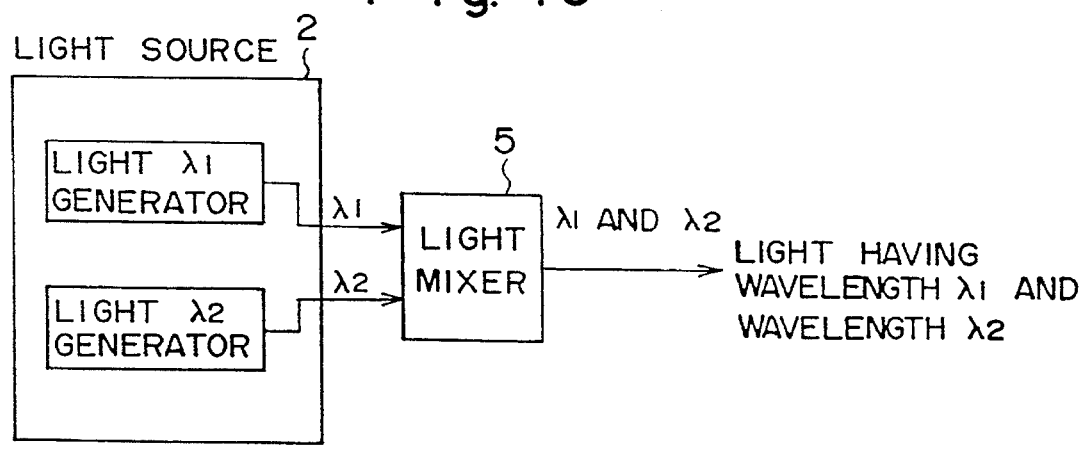
Figure 11:
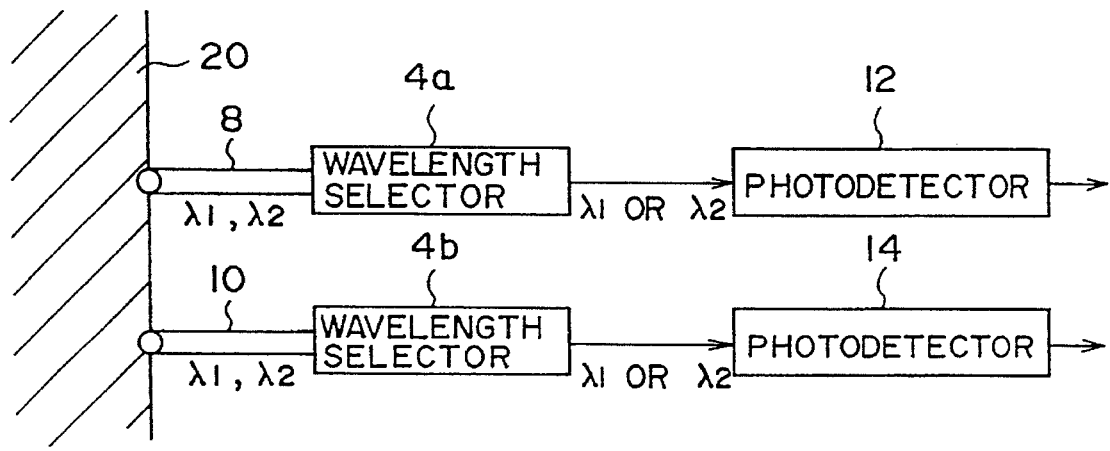
FIGS. 11 and 12 are views respectively showing a configuration of performing detection of light having different wavelengths.
Figure 12:
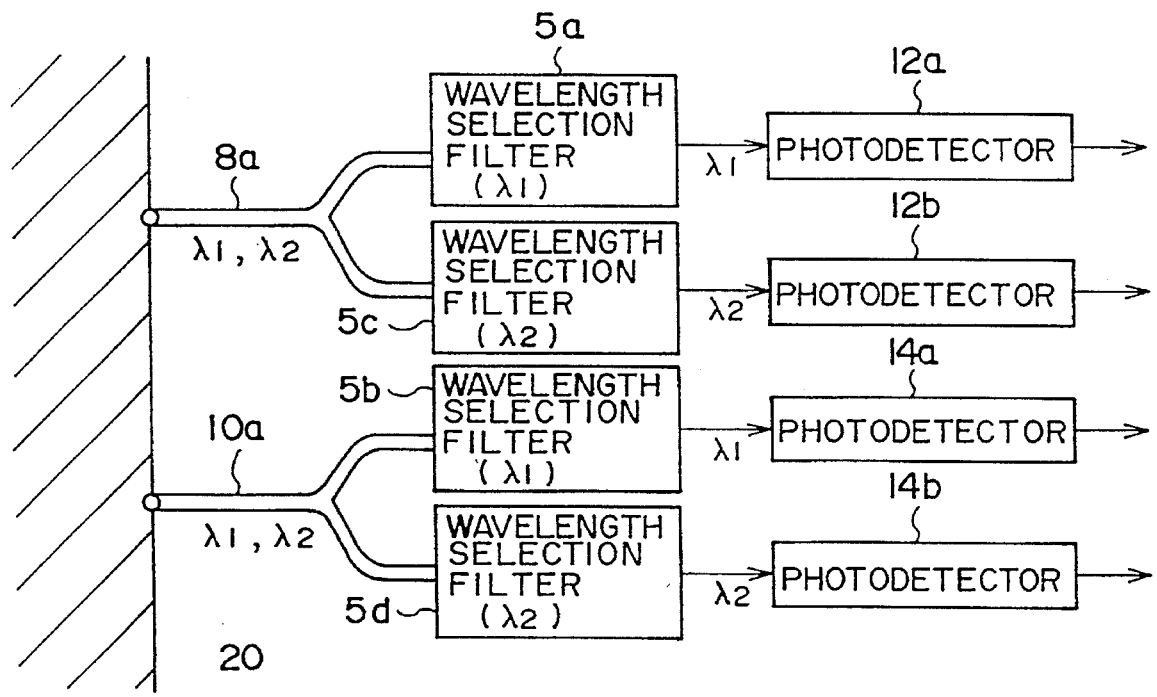

In the above case, there are two methods: a method using light having different wavelengths at the same time; and a method using time-divided light having a different wavelength. As means for selecting a wavelength, there is a method utilizing a light beam selector using a mirror, a wavelength selector using a filter, or a light selector using an optical switch (FIG. 9). In addition, a method of selecting a wavelength by a wavelength selection filter provided in front of a light incident position with lights having different wavelengths being formed into a coaxial beam (FIG. 10), a method of causing lights having different wavelengths to be incident on the scattering medium in parallel and selecting a wavelength by a wavelength selection filter provided in front of the photodetector (FIG. 11), and a method of detecting lights having two kinds of wavelengths at two different points using four photodetectors (FIG. 12) may be used. Moreover, a method of causing light to be incident on two positions is available.

Figure 13:
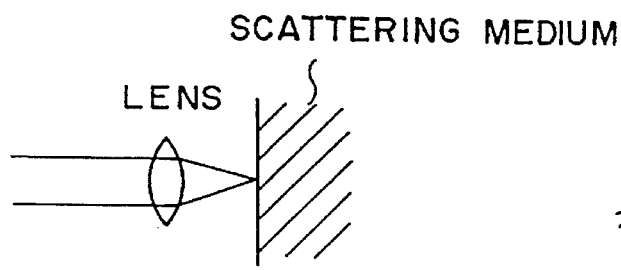
FIGS. 13–16 are views respectively showing a method of causing light to be incident on a scattering medium.
Figure 14:
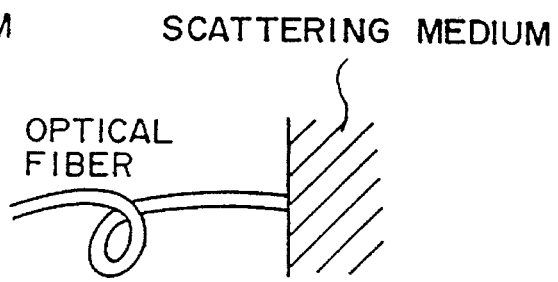
Figure 15:
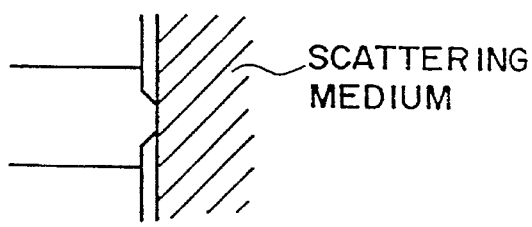
Figure 16:
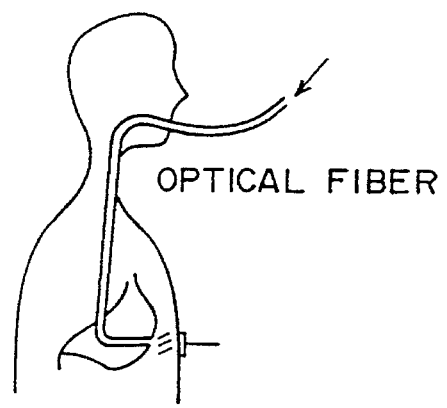
Figure 17:
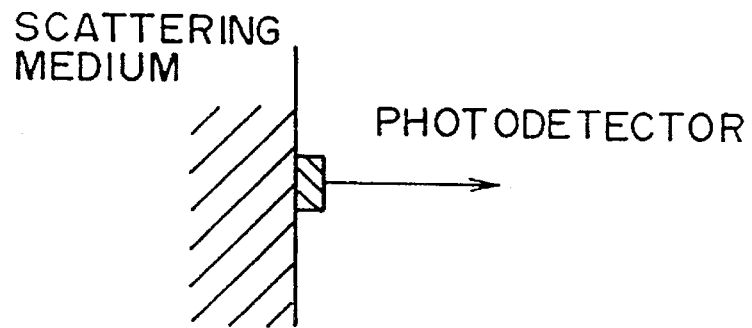
FIGS. 17–19 are views respectively showing a method of receiving light.
Figure 18:
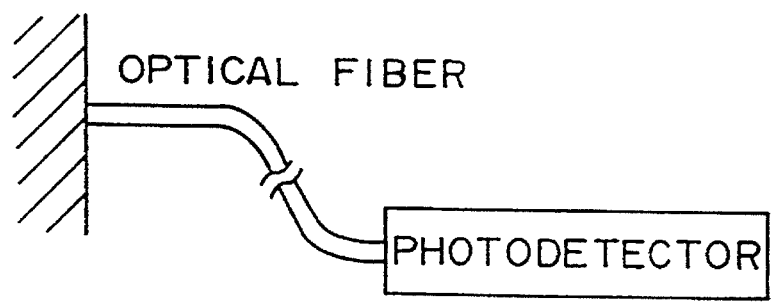
Figure 19:
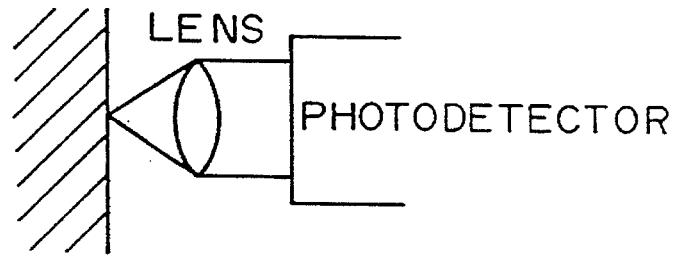

A means for causing the light to be incident on a scattering medium such as a living body may be constituted by a method utilizing a condenser lens (FIG. 13), an optical fiber (FIG. 14), or a pinhole (FIG. 15), or a light incident method using a gastro camera (FIG. 16) or the like, other than the method using light guides as shown in FIG. 8. A means for receiving and detecting the light propagating through the scattering medium may be constituted by a direct photodetection method (FIG. 17), a method of detecting the light through an optical fiber (FIG. 18), a method of detecting light through a lens (FIGS. 19), or the like.

Figure 20:
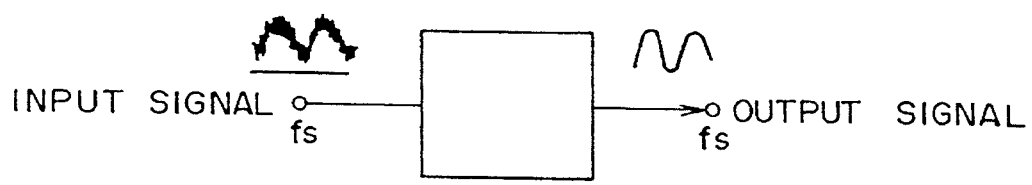
FIGS. 20 and 21 are views respectively showing a method of amplifying detected signals with low noise.
Figure 21:
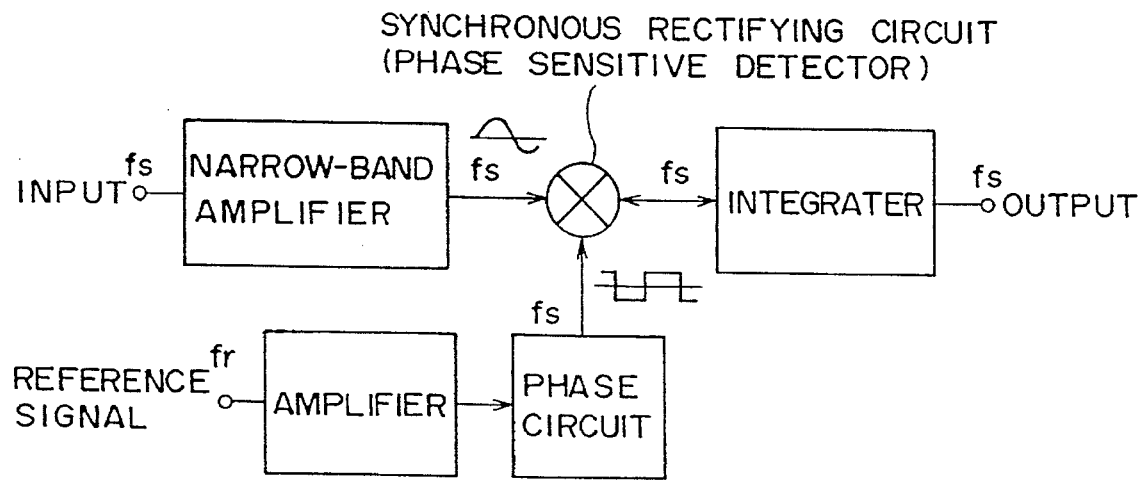

If the signal detected by the photodetector is required to be amplified with low noise, a narrow-band amplifier (FIG. 20), a lock-in amplifier (FIG. 21) or the like can be used. When the lock-in amplifier is used, as a reference signal, the aforementioned synchronizing signal e is utilized. This method is effective for the measurement of a high dynamic range using square wave light or pulsed light. If the absorptive layer is present on the surface of the scattering medium 20 such as a living body specimen, the measurement values c and d can be compensated using the absorption values measured at the position of the detection distances $\rho_1$ and $\rho_2$.

The light incident position and the photodetection points on the scattering medium are concurrently scanned (not shown), and internal information of every location of the scattering medium is obtained and accumulated in a frame memory (not shown), and then read by a TV system, whereby the image showing distribution of internal information can be obtained. If the measurement is performed at different time, the time-change in internal information can be measured. The arithmetic processing unit 16 has a function of storing thus obtained internal information, and a display recording means 18 shown in FIG. 8 displays and/or records these results. The arithmetic processing can be operated at high speed by a computer unit comprising a memory, a display or others.

(2.2) Second Embodiment

Figure 22:
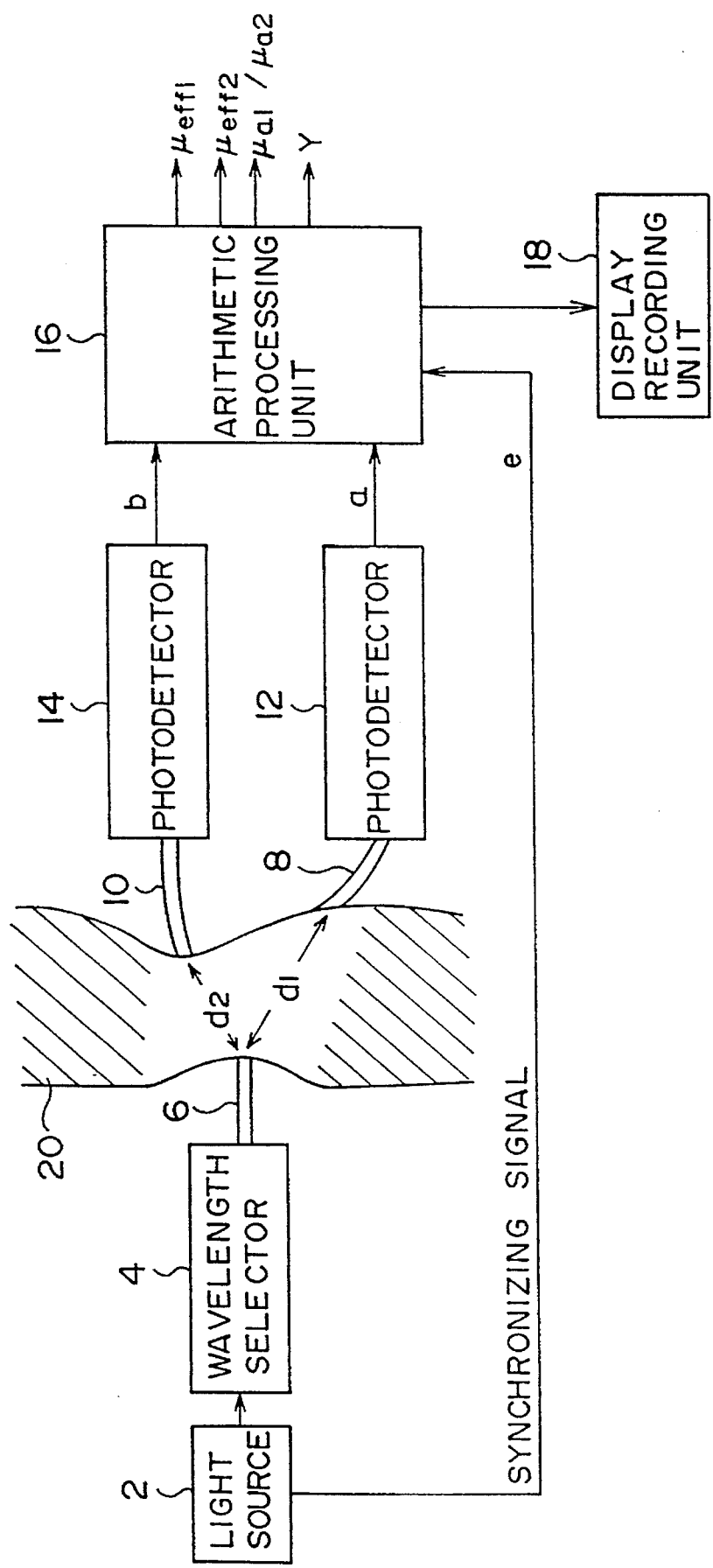
FIG. 22 is a view showing a configuration of an apparatus of the second embodiment.

FIG. 22 illustrates the second structure of the apparatus carrying out the method of measuring internal information in a scattering medium according to the present invention. In this case, the scattering medium is slab like. A light source 2 generates light having different wavelengths $\lambda_1$ and $\lambda_2$. The wavelength of light from the light source 2 is selected by a wavelength selector 4 and light is incident on a surface of a scattering medium 20 which is an object to be measured through a light guide 6. Light diffused during propagation in the scattering medium is received by light guides 8 and 10 provided at positions spaced apart from the light incident position by distances $d_1$ and $d_2$. FIG. 22 shows a state where stress is applied to a part of the scattering medium to be a concave portion so that the distances are $d_1 > d_2$.

The spaces between the light guides 6, 8 and 10 are very small in the embodiment of FIG. 22. In interface material having substantially the same refractive index and scattering coefficient as the object 20 to be measured may be used.

A first photodetector 12 and a second photodetector 14 convert the received optical signals into electric signals, amplify the signals and output the detected signals a and b, respectively. An arithmetic processing unit 16 processes the detected signals a and b from the first detector 12 and the second detector 14, and converts the signals a and b into the measurement values c and d in proportion to the detected quantity of light, respectively. The signal processing is time integration of the detected signals a and b to obtain the measurement values c and d in proportion to the detected quantity of light. In this case, a synchronizing signal e which synchronizes with the operation of the light source 2 or with the operation of the wavelength selector 4 is applied to arithmetic processing unit 16. Note that when the light source 2 generates the square wave light or the pulsed light, the synchronizing signal e may be omitted.

Next, the measurement values c and d at the wavelengths $\lambda_1$ and $\lambda_2$, and the known parameters $\rho_1$ and $\rho_2$ which are set or measured by another method are processed based on the three simultaneous equations to calculate the internal information in the scattering medium, that is, the ratio of absorption coefficients at the wavelength $\lambda_1$ and $\lambda_2$, i.e., $\mu_{a1}/\mu_{a2}$. This sort of arithmetic processing can be operated at high speed by a micro computer installed in the arithmetic processing means. If desired, the degree of oxygen saturation of hemoglobin is calculated using the obtained internal information. If background absorption is present, the light having three or more wavelengths as described above is used.

In the above case, the same as the first embodiment, there are two methods that may be employed: a method using light having different wavelengths at the same time; and a method using time-divided light having a different wavelength. As means for selecting a wavelength, there is a method utilizing a light beam selector using a mirror, a wavelength selector using a filter, or a light selector using an optical switch. In addition, a method of selecting a wavelength by a wavelength selection filter provided in front of a light incident position with lights having different wavelengths being formed into a coaxial beam, a method of causing lights having different wavelengths to be incident on the scattering medium in parallel and selecting a wavelength by a wavelength selection filter provided in front of the photodetector, and a method for detecting light having two wavelengths at two different points using four photodetectors are available.

As a means for causing the light to be incident on a scattering medium, the same method as described in the first embodiment can be used. If the detected signal is needed to be amplified with low noise, a narrow-band amplifier (not shown), a lock-in amplifier (not shown) or the like can be used. The light incident position and the photodetection points on the scattering medium are concurrently scanned (not shown) and internal information of every location of the scattering medium is obtained and accumulated in a frame memory (not shown), and then read by a TV system, whereby the image showing distribution of internal information can be obtained. If the measurement is performed at different time, the time-change in internal information can be measured. The arithmetic processing unit 16 functions to store the thus obtained internal information, and a display recording means 18 shown in FIG. 22 displays and/or records these results. The arithmetic processing can be operated at high speed by a computer unit comprising a memory, a display or others.

To measure a tomogram, scanning is operated along the cross-section of the scattering medium. In this case, rotary scanning of the scattering medium or a pair of light source and photodetector can be performed as in X-ray CT. Rotary scanning may be performed simultaneously with translational scanning. In these cases, if the interface material, which is put in a bag which is doughnut-shaped and which adapts to the shape of the scattering medium, is used to surround the scattering medium 20, rotary scanning can be made easier. In this case, a method of detecting light at a larger number of photodetection points is available.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

What is claimed is:

1. A method of measuring a scattering medium comprising:

emitting light having a plurality of predetermined wavelengths, $\lambda_j$, said wavelengths having transport scattering coefficients, $\mu_s'$, in the scattering medium that are almost equal to each other;

causing said light to be incident on the scattering medium at a light incidence position to propagate said light through the scattering medium;

detecting said light which has propagated through the scattering medium at at least two photodetection points, with distances $\rho_i$, between the light incidence position and each of the photodetection points being different from each other, to obtain at least three detected signals; and extracting internal information of the scattering medium with respect to each of said wavelengths of said light, by converting said at least three detected signals to at least three measured values, $I(\rho_i, \lambda_j)$, and then performing arithmetic processing to said at least three measured values, $I(\rho_i, \lambda_j)$, based on a simultaneous relation of the following equation:

$$\ln(I(\rho_i,\lambda_j)) = \ln(z_0/(2\pi)) - \frac{3}{2} \ln(z_0^2 + \rho_i^2) + \ln(\mu_{\text{eff}j}(z_0^2 + \rho_i^2)^{1/2} + 1) - \mu_{\text{eff}j}(z_0^2 + \rho_i^2)^{1/2}$$

$$[\mu_{\text{eff}j} = (3\mu_{aj}(\mu_{aj} + \mu_s'))^{1/2}]$$

where $I(\rho_i, \lambda_j)$ represents each of the measured values, i is an integer running from one to an integer greater than one, j is an integer running from one to an integer greater than one, $\mu_{\text{eff}j}$ represents an effective attenuation coefficient for light having wavelength $\lambda_j$ $$\mu_{\text{eff}j}=(3\mu_{aj}(\mu_{aj}+\mu_s'))^{1/2},$$

where $\mu_{aj}$ is an absorption coefficient for light having wavelength $\lambda_j$, $\mu_s'$ is the transport scattering coefficient, and $z_0 = 1/\mu_s'$.

2. A method of measuring a scattering medium according to claim 1, wherein said extracting step includes selecting internal information from the group consisting of the effective attenuation coefficients, $\mu_{\text{eff}j}$, and a ratio of the absorption coefficients, $\mu_{aj}$.

3. A method of measuring a scattering medium according to claim 1, wherein said light having the plurality of predetermined wavelengths, $\lambda_j$, of which the absorption coefficients, $\mu_{aj}$, to specified absorptive constituents in said scattering medium are different from each other, said method further comprising the step of:

calculating further internal information with respect to said specified absorptive constituents in said scattering medium by use of the internal information obtained in said extracting step.

4. A method of measuring a scattering medium according to claim 3, wherein said extracting step includes extracting internal information including a ratio of the absorption coefficients, $\mu_{aj}$, with respect to the wavelengths of said light, and a ratio of concentrations of the specified absorptive constituents in the scattering medium.

5. A method of measuring a scattering medium according to claim 1, wherein said three or more detected signals are each detected for a period of time and integrated over said period of time to calculate said three or more measured values, $I(\rho_i, \lambda_j)$.

6. An apparatus for measuring a scattering medium comprising:

light-emitting means for emitting light having a plurality of predetermined wavelengths, $\lambda_j$, said wavelength having transport scattering coefficients, $\mu_s'$, in the scattering medium that are almost equal to each other;

light-incident means for causing said light to be incident on the scattering medium at a light incidence position to propagate said light through the scattering medium;

photodetecting means for detecting said light which has been propagated through the scattering medium at at least two photodetection points, with distances, $\rho_i$, between the light incidence position and each of the photodetection points being different form each other, to obtain at least three detected signals; and first arithmetic processing means for extracting internal information of the scattering medium with respect to each of said wavelengths of said light, by converting said at least three detected signals to at least three measured values, $I(\rho_i, \lambda_j)$, and then performing arithmetic processing to said at least three measured values, $I(\rho_i, \lambda_j)$, based on a simultaneous relation of the following equation:

$$ln(I(\rho_i,\lambda_j))=ln(z_0/(2\pi))-3/2ln(z_0^2+\rho_i^2)+ln(\mu_{\mathit{eff}}(z_0^2+\rho_i^2)^{1/2}+1)-\mu_{\mathit{eff}}(z_0^2+\rho_i^2)^{1/2}$$

where $I(\rho_i, \lambda_j)$ represents each of the measured values, i is an integer running from one to an integer greater than one, j is an integer running from one to an integer greater than one, $\mu_{\mathit{eff}}$ represents an effective attenuation coefficient for light having wavelength $\lambda_j$ $$\mu_{\mathit{eff}}=(3\mu_{aj}(\mu_{aj}+\mu_s'))^{1/2},$$

where $\mu_{aj}$ designates an absorption coefficient for light having wavelength $\lambda_j$, $\mu_s'$ is the transport scattering coefficient, and $z_0=1/\mu_s'$.

7. An apparatus for measuring a scattering medium according to claim 6, wherein said internal information is selected from the group consisting of the effective attenuation coefficients, $\mu_{\mathit{eff}}$, and a ratio of the absorption coefficients, $\mu_{aj}$.

8. An apparatus for measuring a scattering medium according to claim 6, wherein said light having the plurality of predetermined wavelengths, $\lambda_j$, of which the absorption coefficients, $\mu_{aj}$, to specified absorptive constituents in said scattering medium are different from each other, said apparatus further comprising:

second arithmetic processing means for calculating further internal information with respect to said specified absorptive constituents in said scattering medium by use of the internal information obtained in said first arithmetic processing means.

9. An apparatus for measuring a scattering medium according to claim 8, wherein said internal information obtained in said second arithmetic processing means includes a ratio of absorption coefficients, $\mu_{aj}$, with respect to the wavelengths of the said light, and a ratio of concentrations of the specified absorptive constituents in the scattering medium.

10. An apparatus for measuring a scattering medium according to claim 6, wherein said at least three detected signals are each detected for a period of time and integrated over said period of time to calculate said three or more measured values, $I(\rho_i, \lambda_j)$.

11. An apparatus for measuring a scattering medium according to claim 6, wherein said light-incident means is a light guide.

12. An apparatus for measuring a scattering medium comprising:

light-emitting means for emitting light having a plurality of predetermined wavelengths, $\lambda_j$, of which transport scattering coefficients, $\mu_s'$, to the scattering medium are to be almost equal to each other;

light incident means for causing said light to be incident on the scattering medium at a light incidence position to propagate said light through the scattering medium;

photodetecting means for detecting said light which has been propagated through the scattering medium at a plurality of photodetection points, with distances, $\rho_i$, between the light incidence position and each of the photodetection points being different from each other, to obtain at least three detected signals; and arithmetic processing means for extracting internal information of the scattering medium with respect to each of said wavelength of said light used, by converting said at least three detected signals to at least three measured values, $I(\rho_i, \lambda_j)$, and then performing arithmetic processing to said at least three measured values, $I(\rho_i, \lambda_j)$, based on a simultaneous relation of the following equation:

$$ln(I(\rho_i,\lambda_j))=ln(z_0/(2\pi))-3/2ln(z_0^2+\rho_i^2)+ln(\mu_{\mathit{eff}}(z_0^2+\rho_i^2)^{1/2}+1)-\mu_{\mathit{eff}}(z_0^2+\rho_i^2)^{1/2}$$

where $I(\rho_i, \lambda_j)$ represents each of the measured values, i is an integer running from one to an integer greater than two, j is an integer running from one to an integer greater than two, $\mu_{\mathit{eff}}$ represents an effective attenuation coefficient for light having wavelength $\lambda_j$ $$\mu_{\mathit{eff}}=(3\mu_{aj}(\mu_{aj}+\mu_s'))^{1/2},$$

where $\mu_{aj}$ designates an absorption coefficient for light having wavelength $\lambda_j$, and $z_0 = 1/\mu_s'$, wherein said at least three measured values, $I(\rho_i, \lambda_j)$, comprise $I(\rho_1, \lambda_1)$, $I(\rho_2, \lambda_1)$, $I(\rho_1, \lambda_2)$, and $I(\rho_2, \lambda_2)$; and the arithmetic processing means obtains a ratio of absorption coefficient, $\mu_{a1}$, $\mu_{a2}$ as said internal information based on the following equation:

$$\frac{\mu_{a1}}{\mu_{a2}} = \left( \frac{\ln(\rho_1^2 I(\rho_1, \lambda_1)/(\rho_2^2 I(\rho_2, \lambda_1)))}{\ln(\rho_1^2 I(\rho_1, \lambda_2)/(\rho_2^2 I(\rho_2, \lambda_2)))} \right)^2$$

where $\rho_1$, $\rho_2$ are distances between the light incidence position and the photodetection points, $\lambda_1$, $\lambda_2$ are wavelengths of the light used, $\mu_{a1}$ is an absorption coefficient for light having wavelength $\lambda_1$, and $\mu_{a2}$ is an absorption coefficient for light having wavelength $\lambda_2$.

13. A method of measuring a scattering medium comprising:

emitting light having a plurality of predetermined wavelengths, $\lambda_j$, said wavelengths having transport scattering coefficients, $\mu_s'$, in the scattering medium that are almost equal to each other;

causing said light to be incident on the scattering medium at a light incidence position to propagate said light through the scattering medium;

detecting said light which has propagated through the scattering medium at at least two photodetection points, with distances $\rho_i$, between the light incidence position and each of the photodetection points being different from each other, to obtain at least three detected signals; and extracting internal information of the scattering medium with respect to each of said wavelengths of said light, by converting said at least three detected signals to at least three measured values, $I(\rho_i, \lambda_j)$, and then performing arithmetic processing to said at least three measured values, $I(\rho_i, \lambda_j)$, based on a simultaneous relation of the following equation:

$$\ln(I(\rho_i,\lambda_j)) = \ln(z_o/(2\pi)) - 3/2\ln(z_o^2 + \rho_i^2) + \ln(\mu_{eff}(z_o^2+\rho_i^2)^{1/2}+1) - \mu_{eff}(z_o^2+\rho_i^2)^{1/2}$$

where $I(\rho_i, \lambda_j)$ represents each of the measured values, i is an integer running from one to an integer greater than one, j is an integer running from one to an integer greater than one, $\mu_{eff}$ represents an effective attenuation coefficient for light having wavelength $\lambda_j$ $\mu_{eff} = (3\mu_{aj}(\mu_{aj}+\mu_s'))^{1/2}$, where $\mu_{aj}$ is an absorption coefficient for light having wavelength $\lambda_j$, $\mu_s'$ is the transport scattering coefficient, and $z_0 = 1/\mu_s'$ wherein said at least three measured values, $I(\rho_i, \lambda_j)$, comprises $I(\rho_1, \lambda_1)$, $I(\rho_2, \lambda_1)$, $I(\rho_1, \lambda_2)$, and $I(\rho_2, \lambda_2)$; and a ratio of absorption coefficients, $\mu_{a1}$, $\mu_{a2}$ is obtained as said internal information in said extracting step based on the following equation:

$$\frac{\mu_{a1}}{\mu_{a2}} = \left( \frac{\ln(\rho_1^2 I(\rho_1, \lambda_1)/(\rho_2^2 I(\rho_2, \lambda_1)))}{\ln(\rho_1^2 I(\rho_1, \lambda_2)/(\rho_2^2 I(\rho_2, \lambda_2)))} \right)^2$$

where $\rho_1$, $\rho_2$ are distances between the light incidence position and the photodetection points, $\lambda_1$, $\lambda_2$ are wavelengths of the light used, $\mu_{a1}$ is an absorption coefficient for light having wavelength $\lambda_1$, and $\mu_{a2}$ is an absorption coefficient for light having wavelength $\lambda_2$.

* * * * *